(12) United States Patent
Bamdad

(10) Patent No.: US 6,723,517 B1
(45) Date of Patent: Apr. 20, 2004

(54) USE OF SELF-ASSEMBLED MONOLAYERS TO PROBE THE STRUCTURE OF A TARGET MOLECULE

(75) Inventor: Cynthia Carol Bamdad, Newton, MA (US)

(73) Assignee: Minerva Biotechnologies Corporation, Newton, MA (US)

( * ) Notice: Subject to any disclaimer, the term of this patent is extended or adjusted under 35 U.S.C. 154(b) by 0 days.

(21) Appl. No.: 09/324,258

(22) Filed: Jun. 2, 1999

Related U.S. Application Data
(60) Provisional application No. 60/087,766, filed on Jun. 2, 1998.

(51) Int. Cl.[7] ............................................. G01N 33/53
(52) U.S. Cl. ........................ 435/7.1; 436/518; 530/300
(58) Field of Search ........................ 530/300; 436/518; 435/7.1

(56) References Cited

U.S. PATENT DOCUMENTS

| | | | |
|---|---|---|---|
| 5,422,281 A | | 6/1995 | Harris et al. |
| 5,620,850 A | * | 4/1997 | Bamdad ..................... 530/300 |
| 5,716,780 A | | 2/1998 | Edwards et al. |
| 5,744,131 A | | 4/1998 | Edwards et al. |
| 6,180,415 B1 | * | 1/2001 | Schultz et al. .............. 436/518 |
| 6,294,348 B1 | | 9/2001 | Goeddel et al. |
| 6,342,345 B1 | | 1/2002 | Blau et al. |
| 6,384,208 B1 | | 5/2002 | Edwards et al. |
| 6,395,498 B1 | | 5/2002 | Tartaglia et al. |
| 6,416,738 B1 | | 7/2002 | Theodore et al. |
| 6,455,074 B1 | | 9/2002 | Tracy et al. |
| 6,485,987 B1 | | 11/2002 | Charych et al. |

OTHER PUBLICATIONS

Bamdad, Biophys. Journal vol. 75 (Oct. 1998) pp. 1989–1996.*
Lussow et al., Targeting of Antihapten Antibodies . . . , Transplantation, v.62, p. 1703–1708, 1996.*
Ulman, An introduction ot Ultrathin Organic Films . . . , Academic Press, San Diego, p. 288–292, 1991.*
Mrksich et al., Surface Plasmon Resonance . . . , Langmuir, v.11, p. 4383–4385, 1995.*
Sigal et al., A self Assembled Monolayer . . . , Analytical Chemistry, v.66, p. 490–497, 1996.*
Barberis et al., Contact with a Component . . . , Cell, v.81, p. 359–368, 1995.*
Kaufman et al., Effect of Bivalent Interaction . . . , Cancer Research, v.52, p. 4157–4167, 1992.*
Chaiken et al., Analysis of Macromolecular Interactions . . . , Analytical Biochem., v.201(2), p. 197–210, 1992.*
Bamdad, Chynthia Carol, "Novel Surfaces for the Detection and Study of Intermolecular Interactions," A thesis presented by Cynthia Carol Bamdad to The Committee for Higher Degrees in Biophysics in partial fulfillment of the requirements for the degree of Doctor of Philosophy in the subject of Biophysics, Harvard University, Cambridge, Massachusetts. May 1997. pp. 1–111. UMI Dissertation Services, Ann Arbor, MI.
Laibinis, Paul E., Structure of Monolayers Formed by Coadsorption of Two n–Alkanethiols of Different Chain Lengths on Gold and Its Relation to Wetting, J. Phys Chem, 1992, vol. 96, pp. 5097–5105.

* cited by examiner

*Primary Examiner*—Bennett Celsa
(74) *Attorney, Agent, or Firm*—Wolf, Greenfield & Sacks, PC

(57) ABSTRACT

Weak binding motifs were transformed into a high affinity ligand surface by using a heterologous self-assembled monolayer (SAM) as a rigid scaffold to present discrete binding moieties, in a controlled geometry, to a target molecule. At a critical ligand density, the discrete binding moieties simulated a multivalent ligand and promoted high-affinity, cooperative binding of the target molecule. Statistical calculations were applied to SAM components in solution and gold-sulfur packing dimensions to extract the inter-ligand-distance within the SAM. This distance information is valuable to the rational design of multivalent drugs.

31 Claims, 9 Drawing Sheets

$\lambda = (NTA\ concentration)(3\ sites/\ hexagon)(x\ hexagons)$
$\lambda = average\ concentration\ of\ NTA/\ hexagons;\ set\ \lambda = 2;\ solve\ for\ x$ $$x\ hexagons = \frac{2\ NTAs/\ unit\ area}{(NTA\ concentration/\ unit\ volume)(3\ sites/\ hexagon)}$$

| | PROTEIN IMMOBILIZED | MASS IMMOBILIZED (RUs) | PROTEIN IN SOLUTION | MASS CAPTURED (RUs) | RATIO CAPTURED/ IMMOBILIZED |
|---|---|---|---|---|---|
| LOW NTA DENSITY | GST-2X | 1186 | hTBP[124nM] | 5 | 0.004 |
| | GST-4X | 1060 | hTBP[124nM] | 448 | 0.423 |
| HIGH NTA DENSITY | GST-2X | 2080 | hTBP[124nM] | 550 | 0.264 |
| | GST-4X | 2516 | hTBP[124nM] | 1254 | 0.498 |

Fig. 8

| PROTEIN IMMOBILIZED | MASS IMMOBILIZED (RUs) | PROTEIN IN SOLUTION | MASS CAPTURED (RUs) | RATIO | INHIBITION |
|---|---|---|---|---|---|
| GST-4X | 358 | hTBP$_c$ - ALONE | 230 | 0.642 | 0% |
| GST-4X | 438 | hTBP$_c$ + 2X PEPTIDE | 322 | 0.735 | 0% |
| GST-4X | 571 | hTBP$_c$ + 4X PEPTIDE | 0 | 0.000 | 100% |
| GST-2X | 2080 | hTBP$_c$ - ALONE | 550 | 0.264 | 0% |
| GST-2X | 2141 | hTBP$_c$ + 2X PEPTIDE | 556 | 0.259 | 2% |
| GST-2X | 1930 | hTBP$_c$ + 4X PEPTIDE | 51 | 0.026 | 91% |
| GST-4X | 923 | hTBP - ALONE | 600 | 0.650 | 0% |
| GST-4X | 1094 | hTBP + 1X-LINKER-1X | 122 | 0.111 | 83% |
| Gal4-VP16 | 732 | hTBP - ALONE | 483 | 0.659 | 0% |
| Gal4-VP16 | 727 | hTBP + 4x PEPTIDE | 36 | 0.049 | 93% |

Fig. 9

SEQUENCE LISTING

```
<160> NUMBER OF SEQ ID NOS: 20

<210> SEQ ID NO 1
<211> LENGTH: 1876
<212> TYPE: DNA
<213> ORGANISM: Homo sapiens
<220> FEATURE:
<221> NAME/KEY: CDS
<222> LOCATION: (242)...(1261)
<223> OTHER INFORMATION: hTBP

<400> SEQUENCE: 1
cgcggccgcg gttcgctgtg gcgggcgcct gggccgccgg ctgtttaact tcgcttccgc      60
tggcccatag tgatctttgc agtgacccag cagcatcact gtttcttggc gtgtgaagat     120
aacccaagga attgaggaag ttgctgagaa gagtgtgctg gagatgctct aggaaaaaat     180
tgaatagtga gacgagttcc agcgcaaggg tttctggttt gccaagaaga aagtgaacat     240 c atg gat cag aac aac agc ctg cca cct tac gct cag ggc ttg gcc tcc    289
  Met Asp Gln Asn Asn Ser Leu Pro Pro Tyr Ala Gln Gly Leu Ala Ser
    1               5                  10                  15 cct cag ggt gcc atg act ccc gga atc cct atc ttt agt cca atg atg       337
Pro Gln Gly Ala Met Thr Pro Gly Ile Pro Ile Phe Ser Pro Met Met
             20                  25                  30 cct tat ggc act gga ctg acc cca cag cct att cag aac acc aat agt       385
Pro Tyr Gly Thr Gly Leu Thr Pro Gln Pro Ile Gln Asn Thr Asn Ser
         35                  40                  45 ctg tct att ttg gaa gag caa caa agg cag cag cag caa caa caa cag       433
Leu Ser Ile Leu Glu Glu Gln Gln Arg Gln Gln Gln Gln Gln Gln Gln
     50                  55                  60 cag cag cag cag cag cag cag cag caa cag caa cag cag cag cag cag       481
Gln Gln Gln Gln Gln Gln Gln Gln Gln Gln Gln Gln Gln Gln Gln Gln
 65                  70                  75                  80 cag cag cag cag cag cag cag cag cag cag cag cag cag caa cag gca       529
Gln Gln Gln Gln Gln Gln Gln Gln Gln Gln Gln Gln Gln Gln Gln Ala
             85                  90                  95 gtg gca gct gca gcc gtt cag cag tca acg tcc cag cag gca aca cag       577
Val Ala Ala Ala Ala Val Gln Gln Ser Thr Ser Gln Gln Ala Thr Gln
                100                 105                 110 gga acc tca ggc cag gca cca cag ctc ttc cac tca cag act ctc aca       625
Gly Thr Ser Gly Gln Ala Pro Gln Leu Phe His Ser Gln Thr Leu Thr
            115                 120                 125 act gca ccc ttg ccg ggc acc act cca ctg tat ccc tcc ccc atg act       673
Thr Ala Pro Leu Pro Gly Thr Thr Pro Leu Tyr Pro Ser Pro Met Thr
        130                 135                 140 ccc atg acc ccc atc act cct gcc acg cca gct tcg gag agt tct ggg       721
Pro Met Thr Pro Ile Thr Pro Ala Thr Pro Ala Ser Glu Ser Ser Gly
145                 150                 155                 160 att gta ccg cag ctg caa aat att gta tcc aca gtg aat ctt ggt tgt       769
Ile Val Pro Gln Leu Gln Asn Ile Val Ser Thr Val Asn Leu Gly Cys
                165                 170                 175
```

-continued

```
aaa ctt gac cta aag acc att gca ctt cgt gcc cga aac gcc gaa tat      817
Lys Leu Asp Leu Lys Thr Ile Ala Leu Arg Ala Arg Asn Ala Glu Tyr
            180                 185                 190 aat ccc aag cgg ttt gct gcg gta atc atg agg ata aga gag cca cga      865
Asn Pro Lys Arg Phe Ala Ala Val Ile Met Arg Ile Arg Glu Pro Arg
        195                 200                 205 acc acg gca ctg att ttc agt tct ggg aaa atg gtg tgc aca gga gcc      913
Thr Thr Ala Leu Ile Phe Ser Ser Gly Lys Met Val Cys Thr Gly Ala
    210                 215                 220 aag agt gaa gaa cag tcc aga ctg gca gca aga aaa tat gct aga gtt      961
Lys Ser Glu Glu Gln Ser Arg Leu Ala Ala Arg Lys Tyr Ala Arg Val
225                 230                 235                 240 gta cag aag ttg ggt ttt cca gct aag ttc ttg gac ttc aag att cag     1009
Val Gln Lys Leu Gly Phe Pro Ala Lys Phe Leu Asp Phe Lys Ile Gln
                245                 250                 255 aac atg gtg ggg agc tgt gat gtg aag ttt cct ata agg tta gaa ggc     1057
Asn Met Val Gly Ser Cys Asp Val Lys Phe Pro Ile Arg Leu Glu Gly
            260                 265                 270 ctt gtg ctc acc cac caa caa ttt agt agt tat gag cca gag tta ttt     1105
Leu Val Leu Thr His Gln Gln Phe Ser Ser Tyr Glu Pro Glu Leu Phe
        275                 280                 285 cct ggt tta atc tac aga atg atc aaa ccc aga att gtt ctc ctt att     1153
Pro Gly Leu Ile Tyr Arg Met Ile Lys Pro Arg Ile Val Leu Leu Ile
    290                 295                 300 ttt gtt tct gga aaa gtt gta tta aca ggt gct aaa gtc aga gca gaa     1201
Phe Val Ser Gly Lys Val Val Leu Thr Gly Ala Lys Val Arg Ala Glu
305                 310                 315                 320 att tat gaa gca ttt gaa aac atc tac cct att cta aag gga ttc agg     1249
Ile Tyr Glu Ala Phe Glu Asn Ile Tyr Pro Ile Leu Lys Gly Phe Arg
                325                 330                 335 aag acg acg taa tggctctcat gtacccttgc ctcccccacc cccttctttt         1301
Lys Thr Thr * tttttttta aacaaatcag tttgttttgg tacctttaaa tggtggtgtt gtgagaagat    1361
ggatgttgag ttgcagggtg tggcaccagg tgatgcccct ctgtaagtgc ccaccgcggg   1421
atgccgggaa ggggcattat ttgtgcactg agaacaccgc gcagcgtgac tgtgagttgc   1481
tcataccgtg ctgctatctg ggcagcgctg cccatttatt tatatgtaga ttttaaacac   1541
tgctgttgac aagttggttt gagggagaaa actttaagtg ttaaagccac ctctataatt   1601
gattggactt tttaatttta atgttttttcc ccatgaacca cagttttttat atttctacca  1661 gaaaagtaaa aatctttttt aaaagtgttg tttttctaat ttataactcc tagggttat    1721 ttctgtgcca gacacattcc acctctccag tattgcagga cggaatatat gtgttaatga   1781
aaatgaatgg ctgtacatat tttttctttt cttcagagta ctctgtacaa taaatgcagt   1841
ttataaaagt gttaaaaaaa aaaaaaaaaa aaaaa                              1876
```

<210> SEQ ID NO 2
<211> LENGTH: 339
<212> TYPE: PRT
<213> ORGANISM: Homo sapiens

<400> SEQUENCE: 2

```
Met Asp Gln Asn Asn Ser Leu Pro Pro Tyr Ala Gln Gly Leu Ala Ser
  1               5                  10                  15

Pro Gln Gly Ala Met Thr Pro Gly Ile Pro Ile Phe Ser Pro Met Met
            20                  25                  30

Pro Tyr Gly Thr Gly Leu Thr Pro Gln Pro Ile Gln Asn Thr Asn Ser
```

-continued

```
                35                  40                  45
Leu Ser Ile Leu Glu Glu Gln Gln Arg Gln Gln Gln Gln Gln Gln
         50                  55                  60
Gln Gln Gln Gln Gln Gln Gln Gln Gln Gln Gln Gln Gln Gln Gln
 65                  70                  75                  80
Gln Gln Gln Gln Gln Gln Gln Gln Gln Gln Gln Gln Gln Gln Ala
                 85                  90                  95
Val Ala Ala Ala Val Gln Gln Ser Thr Ser Gln Gln Ala Thr Gln
                100                 105                 110
Gly Thr Ser Gly Gln Ala Pro Gln Leu Phe His Ser Gln Thr Leu Thr
             115                 120                 125
Thr Ala Pro Leu Pro Gly Thr Thr Pro Leu Tyr Pro Ser Pro Met Thr
             130                 135                 140
Pro Met Thr Pro Ile Thr Pro Ala Thr Pro Ala Ser Glu Ser Ser Gly
145                 150                 155                 160
Ile Val Pro Gln Leu Gln Asn Ile Val Ser Thr Val Asn Leu Gly Cys
                165                 170                 175
Lys Leu Asp Leu Lys Thr Ile Ala Leu Arg Ala Arg Asn Ala Glu Tyr
             180                 185                 190
Asn Pro Lys Arg Phe Ala Ala Val Ile Met Arg Ile Arg Glu Pro Arg
             195                 200                 205
Thr Thr Ala Leu Ile Phe Ser Ser Gly Lys Met Val Cys Thr Gly Ala
             210                 215                 220
Lys Ser Glu Glu Gln Ser Arg Leu Ala Ala Arg Lys Tyr Ala Arg Val
225                 230                 235                 240
Val Gln Lys Leu Gly Phe Pro Ala Lys Phe Leu Asp Phe Lys Ile Gln
                245                 250                 255
Asn Met Val Gly Ser Cys Asp Val Lys Phe Pro Ile Arg Leu Glu Gly
             260                 265                 270
Leu Val Leu Thr His Gln Gln Phe Ser Ser Tyr Glu Pro Glu Leu Phe
             275                 280                 285
Pro Gly Leu Ile Tyr Arg Met Ile Lys Pro Arg Ile Val Leu Leu Ile
             290                 295                 300
Phe Val Ser Gly Lys Val Val Leu Thr Gly Ala Lys Val Arg Ala Glu
305                 310                 315                 320
Ile Tyr Glu Ala Phe Glu Asn Ile Tyr Pro Ile Leu Lys Gly Phe Arg
                325                 330                 335
Lys Thr Thr
```

<210> SEQ ID NO 3
<211> LENGTH: 181
<212> TYPE: PRT
<213> ORGANISM: Homo sapiens
<220> FEATURE:
<221> NAME/KEY: PEPTIDE
<222> LOCATION: (1)...(181)
<223> OTHER INFORMATION: hTBPc

<400> SEQUENCE: 3

```
Ala Ser Glu Ser Ser Gly Ile Val Pro Gln Leu Gln Asn Ile Val Ser
 1               5                  10                  15
Thr Val Asn Leu Gly Cys Lys Leu Asp Leu Lys Thr Ile Ala Leu Arg
                 20                  25                  30
Ala Arg Asn Ala Glu Tyr Asn Pro Lys Arg Phe Ala Ala Val Ile Met
                 35                  40                  45
```

```
Arg Ile Arg Glu Pro Arg Thr Thr Ala Leu Ile Phe Ser Ser Gly Lys
 50                  55                  60

Met Val Cys Thr Gly Ala Lys Ser Glu Glu Gln Ser Arg Leu Ala Ala
 65                  70                  75                  80

Arg Lys Tyr Ala Arg Val Val Gln Lys Leu Gly Phe Pro Ala Lys Phe
                 85                  90                  95

Leu Asp Phe Lys Ile Gln Asn Met Val Gly Ser Cys Asp Val Lys Phe
            100                 105                 110

Pro Ile Arg Leu Glu Gly Leu Val Leu Thr His Gln Gln Phe Ser Ser
            115                 120                 125

Tyr Glu Pro Glu Leu Phe Pro Gly Leu Ile Tyr Arg Met Ile Lys Pro
130                 135                 140

Arg Ile Val Leu Leu Ile Phe Val Ser Gly Lys Val Val Leu Thr Gly
145                 150                 155                 160

Ala Lys Val Arg Ala Glu Ile Tyr Glu Ala Phe Glu Asn Ile Tyr Pro
                165                 170                 175

Ile Leu Lys Gly Phe
            180

<210> SEQ ID NO 4
<211> LENGTH: 2211
<212> TYPE: DNA
<213> ORGANISM: Herpes simplex virus type 2
<220> FEATURE:
<221> NAME/KEY: CDS
<222> LOCATION: (88)...(1560)
<223> OTHER INFORMATION: VP16

<400> SEQUENCE: 4
ggatccctcc cccctctcc gccgccgggc gctcgggcac gtctcattcg cctctcgaga        60
tcgttattcc cggacccaac cgccccc atg gac ctg ttg gtc gac gat ctg ttt     114
                               Met Asp Leu Leu Val Asp Asp Leu Phe
                                 1               5 gcg gac cgg gac ggg gtt tcg cca ccg ccc ccc agg cca gcc ggg ggt       162
Ala Asp Arg Asp Gly Val Ser Pro Pro Pro Pro Arg Pro Ala Gly Gly
 10                  15                  20                  25 ccc aag aac acc cca gcc gcc cct ccg ctg tac gcc acc ggt cgg ctg       210
Pro Lys Asn Thr Pro Ala Ala Pro Pro Leu Tyr Ala Thr Gly Arg Leu
                 30                  35                  40 agt cag gcc cag ctg atg ccc tcg ccg ccc atg ccc gtc ccc ccc gcg       258
Ser Gln Ala Gln Leu Met Pro Ser Pro Pro Met Pro Val Pro Pro Ala
            45                  50                  55 gcc ctg ttt aac cgt ctc ctc gac gat ctg ggc ttc agc gcg ggt ccc       306
Ala Leu Phe Asn Arg Leu Leu Asp Asp Leu Gly Phe Ser Ala Gly Pro
            60                  65                  70 gcg ctg tgt acc atg cta gat acc tgg aac gag gac ctg ttc tct ggg       354
Ala Leu Cys Thr Met Leu Asp Thr Trp Asn Glu Asp Leu Phe Ser Gly
 75                  80                  85 ttc ccg acc aac gcc gac atg tac cgg gag tgc aag ttt ctg tcg acg       402
Phe Pro Thr Asn Ala Asp Met Tyr Arg Glu Cys Lys Phe Leu Ser Thr
 90                  95                 100                 105 ctg ccc agc gac gtg atc gac tgg ggg gat gcg cac gtc ccc gag cgc       450
Leu Pro Ser Asp Val Ile Asp Trp Gly Asp Ala His Val Pro Glu Arg
                110                 115                 120 tcc ccg atc gac att cgc gcc cac ggc gac gtg gcg ttc ccc acc ctg       498
Ser Pro Ile Asp Ile Arg Ala His Gly Asp Val Ala Phe Pro Thr Leu
            125                 130                 135 ccc gcc acc cgc gac gag ctg cct tcg tac tac gag gcc atg gcg cag       546
Pro Ala Thr Arg Asp Glu Leu Pro Ser Tyr Tyr Glu Ala Met Ala Gln
```

-continued

```
                140                 145                 150
ttt ttc cgc ggt gag ctg cgg gcg cgg gag gag agc tac cgg acc gtg    594
Phe Phe Arg Gly Glu Leu Arg Ala Arg Glu Glu Ser Tyr Arg Thr Val
    155                 160                 165 ttg gca aat ttt tgc tcg gcc ctg tac cgg tac ctg cgc gcc agc gtt    642
Leu Ala Asn Phe Cys Ser Ala Leu Tyr Arg Tyr Leu Arg Ala Ser Val
170                 175                 180                 185 cgg cag cta cac cgc cag gca cac atg cgg ggc cgc aac cgc gac ctg    690
Arg Gln Leu His Arg Gln Ala His Met Arg Gly Arg Asn Arg Asp Leu
                190                 195                 200 cgg gag atg ctg cgc acc acg atc gcg gac agg tac tac cgc gag acc    738
Arg Glu Met Leu Arg Thr Thr Ile Ala Asp Arg Tyr Tyr Arg Glu Thr
            205                 210                 215 gcg cgc ctg gcg cgc gtc ctg ttt ctg cat cta tac ctc ttt ctg agc    786
Ala Arg Leu Ala Arg Val Leu Phe Leu His Leu Tyr Leu Phe Leu Ser
        220                 225                 230 cgc gag atc cta tgg gcc gcg tac gcc gag cag atg atg cgg ccc gat    834
Arg Glu Ile Leu Trp Ala Ala Tyr Ala Glu Gln Met Met Arg Pro Asp
    235                 240                 245 ctg ttc gac ggc ctc tgc tgc gac ctg gag agc tgg cgc cag ttg gcg    882
Leu Phe Asp Gly Leu Cys Cys Asp Leu Glu Ser Trp Arg Gln Leu Ala
250                 255                 260                 265 tgt ctg ttt cag ccc ctg atg ttt atc aac gga tcg ctc acc gtg cgg    930
Cys Leu Phe Gln Pro Leu Met Phe Ile Asn Gly Ser Leu Thr Val Arg
                270                 275                 280 gga gtt ccc gtg gag gcc cgg cga ctg cgg gag cta aac cac att cgc    978
Gly Val Pro Val Glu Ala Arg Arg Leu Arg Glu Leu Asn His Ile Arg
            285                 290                 295 gag cac ctg aac ctc ccg ctg gtg cga agt gcg gcg gcg gag gaa ccc    1026
Glu His Leu Asn Leu Pro Leu Val Arg Ser Ala Ala Ala Glu Glu Pro
        300                 305                 310 ggg gcg ccc ctc acg acc ccg ccc gtc ctg cag ggc aac cag gcc cgc    1074
Gly Ala Pro Leu Thr Thr Pro Pro Val Leu Gln Gly Asn Gln Ala Arg
    315                 320                 325 tcc tct ggg tac ttt atg ctg ctg atc cgg gcc aag ttg gac tcg tac    1122
Ser Ser Gly Tyr Phe Met Leu Leu Ile Arg Ala Lys Leu Asp Ser Tyr
330                 335                 340                 345 tcc agc gtc gcg acc tcg gag ggc gag tcc gtc atg cgg gag cac gcg    1170
Ser Ser Val Ala Thr Ser Glu Gly Glu Ser Val Met Arg Glu His Ala
                350                 355                 360 tat agc cgc ggg cgg acc aga aac aat tac gga tcg aca atc gag ggc    1218
Tyr Ser Arg Gly Arg Thr Arg Asn Asn Tyr Gly Ser Thr Ile Glu Gly
            365                 370                 375 ctg ctc gac ctc ccg gac gac gat gac gct cct gcg gag gcc ggg ctg    1266
Leu Leu Asp Leu Pro Asp Asp Asp Asp Ala Pro Ala Glu Ala Gly Leu
        380                 385                 390 gtg gcg ccg cgc atg tcg ttt ctc tcc gcg gga caa cgc ccc cgc aga    1314
Val Ala Pro Arg Met Ser Phe Leu Ser Ala Gly Gln Arg Pro Arg Arg
    395                 400                 405 ctg tcc acc acc gcc ccc att acc gac gtc agc ctg gga gac gaa ctc    1362
Leu Ser Thr Thr Ala Pro Ile Thr Asp Val Ser Leu Gly Asp Glu Leu
410                 415                 420                 425 cgc ctg gac ggc gag gag gtg gat atg acg ccc gcc gac gcc ctg gac    1410
Arg Leu Asp Gly Glu Glu Val Asp Met Thr Pro Ala Asp Ala Leu Asp
                430                 435                 440 gac ttc gac ttg gag atg ctg ggg gac gtg gag tcc ccc tcc ccg gga    1458
Asp Phe Asp Leu Glu Met Leu Gly Asp Val Glu Ser Pro Ser Pro Gly
            445                 450                 455 atg acc cac gac ccc gtc tcg tat ggg gct ttg gac gtg gac gat ttt    1506
```

-continued

```
              Met Thr His Asp Pro Val Ser Tyr Gly Ala Leu Asp Val Asp Phe
                      460                 465                 470 gag ttt gaa cag atg ttt acc gat gcc atg ggc att gac gac ttt ggg        1554
Glu Phe Glu Gln Met Phe Thr Asp Ala Met Gly Ile Asp Asp Phe Gly
        475                 480                 485 ggg tag gatgtgcgac cgggcggcgc gccccccccc caccaccgcc ccgcctcacc        1610
Gly *
490 tccgtctgta tcgcgataga gggttcgcaa ccacagcaat aaacattggc aagcaactca        1670
tcatacgcgg cgtgcgttgg ctgtttatta cgggaccatg aaagaaatgg ggttacgcgc        1730
ggggtggggg gtgtgtgccg ttgggttggg cgttagtcgc gcctacgagc ccgcggtcgt        1790
gtagattcgc gtcacagaac ggctcgtggt gctgggtcc gcgtataaag gcaggcgcgc        1850
gggtcccgtt ctcgcatttg cccgcgggtc tgcgtgggga cgaggcccac cccccaccc        1910
ttgttggagc ggtcgcgttt tctctgttcc cgtcgtgccg gttcctaccc cccgctccct        1970
gggaccgccc cctaccccc acctcccgt ttgggcctcc cccctcgcac caccccttc        2030
ctcgtccgtc tgcggggagg gcgtgtgtaa aaaatcgggc ctccggccac catgtccgtg        2090
cgcgggcatg ccgtacgccg gaggcgcgcc tccacccggt cccatgcccc gtccgcgcat        2150
cgcgccgact cgcccgtgga ggacgagccc gagggcggtg gagtcgggtt aatggggtac        2210
c                                                                       2211

<210> SEQ ID NO 5
<211> LENGTH: 490
<212> TYPE: PRT
<213> ORGANISM: Herpes simplex virus type 2

<400> SEQUENCE: 5

Met Asp Leu Leu Val Asp Asp Leu Phe Ala Asp Arg Asp Gly Val Ser
  1               5                  10                  15

Pro Pro Pro Pro Arg Pro Ala Gly Gly Pro Lys Asn Thr Pro Ala Ala
                 20                  25                  30

Pro Pro Leu Tyr Ala Thr Gly Arg Leu Ser Gln Ala Gln Leu Met Pro
         35                  40                  45

Ser Pro Pro Met Pro Val Pro Pro Ala Ala Leu Phe Asn Arg Leu Leu
 50                  55                  60

Asp Asp Leu Gly Phe Ser Ala Gly Pro Ala Leu Cys Thr Met Leu Asp
 65                  70                  75                  80

Thr Trp Asn Glu Asp Leu Phe Ser Gly Phe Pro Thr Asn Ala Asp Met
                 85                  90                  95

Tyr Arg Glu Cys Lys Phe Leu Ser Thr Leu Pro Ser Asp Val Ile Asp
                100                 105                 110

Trp Gly Asp Ala His Val Pro Glu Arg Ser Pro Ile Asp Ile Arg Ala
        115                 120                 125

His Gly Asp Val Ala Phe Pro Thr Leu Pro Ala Thr Arg Asp Glu Leu
130                 135                 140

Pro Ser Tyr Tyr Glu Ala Met Ala Gln Phe Phe Arg Gly Glu Leu Arg
145                 150                 155                 160

Ala Arg Glu Glu Ser Tyr Arg Thr Val Leu Ala Asn Phe Cys Ser Ala
                165                 170                 175

Leu Tyr Arg Tyr Leu Arg Ala Ser Val Arg Gln Leu His Arg Gln Ala
                180                 185                 190

His Met Arg Gly Arg Asn Arg Asp Leu Arg Glu Met Leu Arg Thr Thr
        195                 200                 205
```

```
Ile Ala Asp Arg Tyr Tyr Arg Glu Thr Ala Arg Leu Ala Arg Val Leu
    210                 215                 220
Phe Leu His Leu Tyr Leu Phe Leu Ser Arg Glu Ile Leu Trp Ala Ala
225                 230                 235                 240
Tyr Ala Glu Gln Met Met Arg Pro Asp Leu Phe Asp Gly Leu Cys Cys
                245                 250                 255
Asp Leu Glu Ser Trp Arg Gln Leu Ala Cys Leu Phe Gln Pro Leu Met
            260                 265                 270
Phe Ile Asn Gly Ser Leu Thr Val Arg Gly Val Pro Val Glu Ala Arg
        275                 280                 285
Arg Leu Arg Glu Leu Asn His Ile Arg Glu His Leu Asn Leu Pro Leu
    290                 295                 300
Val Arg Ser Ala Ala Ala Glu Glu Pro Gly Ala Pro Leu Thr Thr Pro
305                 310                 315                 320
Pro Val Leu Gln Gly Asn Gln Ala Arg Ser Ser Gly Tyr Phe Met Leu
                325                 330                 335
Leu Ile Arg Ala Lys Leu Asp Ser Tyr Ser Ser Val Ala Thr Ser Glu
            340                 345                 350
Gly Glu Ser Val Met Arg Glu His Ala Tyr Ser Arg Gly Arg Thr Arg
        355                 360                 365
Asn Asn Tyr Gly Ser Thr Ile Glu Gly Leu Leu Asp Leu Pro Asp Asp
    370                 375                 380
Asp Asp Ala Pro Ala Glu Ala Gly Leu Val Ala Pro Arg Met Ser Phe
385                 390                 395                 400
Leu Ser Ala Gly Gln Arg Pro Arg Arg Leu Ser Thr Thr Ala Pro Ile
                405                 410                 415
Thr Asp Val Ser Leu Gly Asp Glu Leu Arg Leu Asp Gly Glu Glu Val
            420                 425                 430
Asp Met Thr Pro Ala Asp Ala Leu Asp Asp Phe Asp Leu Glu Met Leu
        435                 440                 445
Gly Asp Val Glu Ser Pro Ser Pro Gly Met Thr His Asp Pro Val Ser
    450                 455                 460
Tyr Gly Ala Leu Asp Val Asp Asp Phe Glu Phe Glu Gln Met Phe Thr
465                 470                 475                 480
Asp Ala Met Gly Ile Asp Asp Phe Gly Gly
                485                 490

<210> SEQ ID NO 6
<211> LENGTH: 3694
<212> TYPE: DNA
<213> ORGANISM: Saccharomyces cerevisiae
<220> FEATURE:
<221> NAME/KEY: CDS
<222> LOCATION: (443)...(3088)
<223> OTHER INFORMATION: GAL4

<400> SEQUENCE: 6
gatcccttaa gtttaaacaa caacagcaag caggtgtgca agacactaga gactcctaac      60
atgatgtatg ccaataaaac acaagagata acaacattg catggaggcc ccagaggggc     120
gattggtttg ggtgcgtgag cggcaagaag tttcaaaacg tccgcgtcct ttgagacagc     180
attcgcccag tattttttt attctacaaa ccttctataa tttcaaagta tttacataat     240
tctgtatcag tttaatcacc ataatatcgt tttctttgtt tagtgcaatt aattttttcct   300 attgttactt cgggcctttt tctgttttat gagctatttt ttccgtcatc cttccccaga     360
```

```
                                            -continued ttttcagctt catctccaga ttgtgtctac gtaatgcacg ccatcatttt aagagaggac    420
agagaagcaa gcctcctgaa ag atg aag cta ctg tct tct atc gaa caa gca    472
                        Met Lys Leu Leu Ser Ser Ile Glu Gln Ala
                         1               5                    10 tgc gat att tgc cga ctt aaa aag ctc aag tgc tcc aaa gaa aaa ccg    520
Cys Asp Ile Cys Arg Leu Lys Lys Leu Lys Cys Ser Lys Glu Lys Pro
             15                  20                  25 aag tgc gcc aag tgt ctg aag aac aac tgg gag tgt cgc tac tct ccc    568
Lys Cys Ala Lys Cys Leu Lys Asn Asn Trp Glu Cys Arg Tyr Ser Pro
             30                  35                  40 aaa acc aaa agg tct ccg ctg act agg gca cat ctg aca gaa gtg gaa    616
Lys Thr Lys Arg Ser Pro Leu Thr Arg Ala His Leu Thr Glu Val Glu
             45                  50                  55 tca agg cta gaa aga ctg gaa cag cta ttt cta ctg att ttt cct cga    664
Ser Arg Leu Glu Arg Leu Glu Gln Leu Phe Leu Leu Ile Phe Pro Arg
         60                  65                  70 gaa gac ctt gac atg att ttg aaa atg gat tct tta cag gat ata aaa    712
Glu Asp Leu Asp Met Ile Leu Lys Met Asp Ser Leu Gln Asp Ile Lys
 75                  80                  85                  90 gca ttg tta aca gga tta ttt gta caa gat aat gtg aat aaa gat gcc    760
Ala Leu Leu Thr Gly Leu Phe Val Gln Asp Asn Val Asn Lys Asp Ala
                 95                 100                 105 gtc aca gat aga ttg gct tca gtg gag act gat atg cct cta aca ttg    808
Val Thr Asp Arg Leu Ala Ser Val Glu Thr Asp Met Pro Leu Thr Leu
             110                 115                 120 aga cag cat aga ata agt gcg aca tca tca tcg gaa gag agt agt aac    856
Arg Gln His Arg Ile Ser Ala Thr Ser Ser Ser Glu Glu Ser Ser Asn
             125                 130                 135 aaa ggt caa aga cag ttg act gta tcg att gac tcg gca gct cat cat    904
Lys Gly Gln Arg Gln Leu Thr Val Ser Ile Asp Ser Ala Ala His His
140                 145                 150 gat aac tcc aca att ccg ttg gat ttt atg ccc agg gat gct ctt cat    952
Asp Asn Ser Thr Ile Pro Leu Asp Phe Met Pro Arg Asp Ala Leu His
155                 160                 165                 170 gga ttt gat tgg tct gaa gag gat gac atg tcg gat ggc ttg ccc ttc   1000
Gly Phe Asp Trp Ser Glu Glu Asp Asp Met Ser Asp Gly Leu Pro Phe
                 175                 180                 185 ctg aaa acg gac ccc aac aat aat ggg ttc ttt ggc gac ggt tct ctc   1048
Leu Lys Thr Asp Pro Asn Asn Asn Gly Phe Phe Gly Asp Gly Ser Leu
             190                 195                 200 tta tgt att ctt cga tct att ggc ttt aaa ccg gaa aat tac acg aac   1096
Leu Cys Ile Leu Arg Ser Ile Gly Phe Lys Pro Glu Asn Tyr Thr Asn
             205                 210                 215 tct aac gtt aac agg ctc ccg acc atg att acg gat aga tac acg ttg   1144
Ser Asn Val Asn Arg Leu Pro Thr Met Ile Thr Asp Arg Tyr Thr Leu
     220                 225                 230 gct tct aga tcc aca aca tcc cgt tta ctt caa agt tat ctc aat aat   1192
Ala Ser Arg Ser Thr Thr Ser Arg Leu Leu Gln Ser Tyr Leu Asn Asn
235                 240                 245                 250 ttt cac ccc tac tgc cct atc gtg cac tca ccg acg cta atg atg ttg   1240
Phe His Pro Tyr Cys Pro Ile Val His Ser Pro Thr Leu Met Met Leu
                 255                 260                 265 tat aat aac cag att gaa atc gcg tcg aag gat caa tgg caa atc ctt   1288
Tyr Asn Asn Gln Ile Glu Ile Ala Ser Lys Asp Gln Trp Gln Ile Leu
                 270                 275                 280 ttt aac tgc ata tta gcc att gga gcc tgg tgt ata gag ggg gaa tct   1336
Phe Asn Cys Ile Leu Ala Ile Gly Ala Trp Cys Ile Glu Gly Glu Ser
             285                 290                 295 act gat ata gat gtt ttt tac tat caa aat gct aaa tct cat ttg acg   1384
```

```
                                                              -continued

Thr Asp Ile Asp Val Phe Tyr Tyr Gln Asn Ala Lys Ser His Leu Thr
    300                 305                 310 agc aag gtc ttc gag tca ggt tcc ata att ttg gtg aca gcc cta cat    1432
Ser Lys Val Phe Glu Ser Gly Ser Ile Ile Leu Val Thr Ala Leu His
315                 320                 325                 330 ctt ctg tcg cga tat aca cag tgg agg cag aaa aca aat act agc tat    1480
Leu Leu Ser Arg Tyr Thr Gln Trp Arg Gln Lys Thr Asn Thr Ser Tyr
                335                 340                 345 aat ttt cac agc ttt tcc ata aga atg gcc ata tca ttg ggc ttg aat    1528
Asn Phe His Ser Phe Ser Ile Arg Met Ala Ile Ser Leu Gly Leu Asn
            350                 355                 360 agg gac ctc ccc tcg tcc ttc agt gat agc agc att ctg gaa caa aga    1576
Arg Asp Leu Pro Ser Ser Phe Ser Asp Ser Ser Ile Leu Glu Gln Arg
        365                 370                 375 cgc cga att tgg tgg tct gtc tac tct tgg gag atc caa ttg tcc ctg    1624
Arg Arg Ile Trp Trp Ser Val Tyr Ser Trp Glu Ile Gln Leu Ser Leu
    380                 385                 390 ctt tat ggt cga tcc atc cag ctt tct cag aat aca atc tcc ttc cct    1672
Leu Tyr Gly Arg Ser Ile Gln Leu Ser Gln Asn Thr Ile Ser Phe Pro
395                 400                 405                 410 tct tct gtc gac gat gtg cag cgt acc aca aca ggt ccc acc ata tat    1720
Ser Ser Val Asp Asp Val Gln Arg Thr Thr Thr Gly Pro Thr Ile Tyr
                415                 420                 425 cat ggc atc att gaa aca gca agg ctc tta caa gtt ttc aca aaa atc    1768
His Gly Ile Ile Glu Thr Ala Arg Leu Leu Gln Val Phe Thr Lys Ile
            430                 435                 440 tat gaa cta gac aaa aca gta act gca gaa aaa agt cct ata tgt gca    1816
Tyr Glu Leu Asp Lys Thr Val Thr Ala Glu Lys Ser Pro Ile Cys Ala
        445                 450                 455 aaa aaa tgc ttg atg att tgt aat gag att gag gag gtt tcg aga cag    1864
Lys Lys Cys Leu Met Ile Cys Asn Glu Ile Glu Glu Val Ser Arg Gln
    460                 465                 470 gca cca aag ttt tta caa atg gat att tcc acc acc gct cta acc aat    1912
Ala Pro Lys Phe Leu Gln Met Asp Ile Ser Thr Thr Ala Leu Thr Asn
475                 480                 485                 490 ttg ttg aag gaa cac cct tgg cta tcc ttt aca aga ttc gaa ctg aag    1960
Leu Leu Lys Glu His Pro Trp Leu Ser Phe Thr Arg Phe Glu Leu Lys
                495                 500                 505 tgg aaa cag ttg tct ctt atc att tat gta tta aga gat ttt ttc act    2008
Trp Lys Gln Leu Ser Leu Ile Ile Tyr Val Leu Arg Asp Phe Phe Thr
            510                 515                 520 aat ttt acc cag aaa aag tca caa cta gaa cag gat caa aat gat cat    2056
Asn Phe Thr Gln Lys Lys Ser Gln Leu Glu Gln Asp Gln Asn Asp His
        525                 530                 535 caa agt tat gaa gtt aaa cga tgc tcc atc atg tta agc gat gca gca    2104
Gln Ser Tyr Glu Val Lys Arg Cys Ser Ile Met Leu Ser Asp Ala Ala
    540                 545                 550 caa aga act gtt atg tct gta agt agc tat atg gac aat cat aat gtc    2152
Gln Arg Thr Val Met Ser Val Ser Ser Tyr Met Asp Asn His Asn Val
555                 560                 565                 570 acc cca tat ttt gcc tgg aat tgt tct tat tac ttg ttc aat gca gtc    2200
Thr Pro Tyr Phe Ala Trp Asn Cys Ser Tyr Tyr Leu Phe Asn Ala Val
                575                 580                 585 cta gta ccc ata aag act cta ctc tca aac tca aaa tcg aat gct gag    2248
Leu Val Pro Ile Lys Thr Leu Leu Ser Asn Ser Lys Ser Asn Ala Glu
            590                 595                 600 aat aac gag acc gca caa tta tta caa caa att aac act gtt ctg atg    2296
Asn Asn Glu Thr Ala Gln Leu Leu Gln Gln Ile Asn Thr Val Leu Met
        605                 610                 615
```

```
cta tta aaa aaa ctg gcc act ttt aaa atc cag act tgt gaa aaa tac      2344
Leu Leu Lys Lys Leu Ala Thr Phe Lys Ile Gln Thr Cys Glu Lys Tyr
    620                 625                 630 att caa gta ctg gaa gag gta tgt gcg ccg ttt ctg tta tca cag tgt      2392
Ile Gln Val Leu Glu Glu Val Cys Ala Pro Phe Leu Leu Ser Gln Cys
635                 640                 645                 650 gca atc cca tta ccg cat atc agt tat aac aat agt aat ggt agc gcc      2440
Ala Ile Pro Leu Pro His Ile Ser Tyr Asn Asn Ser Asn Gly Ser Ala
                655                 660                 665 att aaa aat att gtc ggt tct gca act atc gcc caa tac cct act ctt      2488
Ile Lys Asn Ile Val Gly Ser Ala Thr Ile Ala Gln Tyr Pro Thr Leu
    670                 675                 680 ccg gag gaa aat gtc aac aat atc agt gtt aaa tat gtt tct cct ggc      2536
Pro Glu Glu Asn Val Asn Asn Ile Ser Val Lys Tyr Val Ser Pro Gly
685                 690                 695 tca gta ggg cct tca cct gtg cca ttg aaa tca gga gca agt ttc agt      2584
Ser Val Gly Pro Ser Pro Val Pro Leu Lys Ser Gly Ala Ser Phe Ser
                700                 705                 710 gat cta gtc aag ctg tta tct aac cgt cca ccc tct cgt aac tct cca      2632
Asp Leu Val Lys Leu Leu Ser Asn Arg Pro Pro Ser Arg Asn Ser Pro
715                 720                 725                 730 gtg aca ata cca aga agc aca cct tcg cat cgc tca gtc acg cct ttt      2680
Val Thr Ile Pro Arg Ser Thr Pro Ser His Arg Ser Val Thr Pro Phe
                735                 740                 745 cta ggg caa cag caa cag ctg caa tca tta gtg cca ctg acc ccg tct      2728
Leu Gly Gln Gln Gln Gln Leu Gln Ser Leu Val Pro Leu Thr Pro Ser
    750                 755                 760 gct ttg ttt ggt ggc gcc aat ttt aat caa agt ggg aat att gct gat      2776
Ala Leu Phe Gly Gly Ala Asn Phe Asn Gln Ser Gly Asn Ile Ala Asp
            765                 770                 775 agc tca ttg tcc ttc act ttc act aac agt agc aac ggt ccg aac ctc      2824
Ser Ser Leu Ser Phe Thr Phe Thr Asn Ser Ser Asn Gly Pro Asn Leu
780                 785                 790 ata aca act caa aca aat tct caa gcg ctt tca caa cca att gcc tcc      2872
Ile Thr Thr Gln Thr Asn Ser Gln Ala Leu Ser Gln Pro Ile Ala Ser
795                 800                 805                 810 tct aac gtt cat gat aac ttc atg aat aat gaa atc acg gct agt aaa      2920
Ser Asn Val His Asp Asn Phe Met Asn Asn Glu Ile Thr Ala Ser Lys
                815                 820                 825 att gat gat ggt aat aat tca aaa cca ctg tca cct ggt tgg acg gac      2968
Ile Asp Asp Gly Asn Asn Ser Lys Pro Leu Ser Pro Gly Trp Thr Asp
    830                 835                 840 caa act gcg tat aac gcg ttt gga atc act aca ggg atg ttt aat acc      3016
Gln Thr Ala Tyr Asn Ala Phe Gly Ile Thr Thr Gly Met Phe Asn Thr
            845                 850                 855 act aca atg gat gat gta tat aac tat cta ttc gat gat gaa gat acc      3064
Thr Thr Met Asp Asp Val Tyr Asn Tyr Leu Phe Asp Asp Glu Asp Thr
860                 865                 870 cca cca aac cca aaa aaa gag taa atgaatcgt agatactgaa aaccccgca       3118
Pro Pro Asn Pro Lys Lys Glu  *
875                 880 agttcacttc aactgtgcat cgtgcaccat ctcaatttct ttcatttata catcgttttg     3178
ccttctttta tgtaactata ctcctctaag tttcaatctt ggccatgtaa cctctgatct     3238
atagaatttt ttaaatgact agaattaatg cccatctttt ttttggacct aaattcttca     3298
tgaaaatata ttacgagggc ttattcagaa gcttcgctca tataacgaaa aaaagggtt     3358 tggatcgaac gtaattgaga ttgattagtt aatactcaaa ataaaacagc tcctaccacc     3418
agtgtaaagt agaacgttaa tagagcaatg tcttcagaca aatctattga gaaaaataca     3478
```

-continued

```
gatacgatcg cctctgaagt tcacgaaggt gataatcatt cgaataattt gggttcaatg    3538
gaggaagaga taaaatcaac gccatcagac caatatgaag agatagctat aattccaact    3598
gagcccctcc attcggacaa agaactaaat gacaagcaac aaagtttagg ccatgaagca    3658
cccacaaatg tatcaagaga agaacctatt gggatc                              3694
```

<210> SEQ ID NO 7
<211> LENGTH: 881
<212> TYPE: PRT
<213> ORGANISM: Saccharomyces cerevisiae

<400> SEQUENCE: 7

```
Met Lys Leu Leu Ser Ser Ile Glu Gln Ala Cys Asp Ile Cys Arg Leu
 1               5                  10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Ile Asp Ser Ala Ala His His Asp Asn Ser Thr Ile Pro
145                 150                 155                 160

Leu Asp Phe Met Pro Arg Asp Ala Leu His Gly Phe Asp Trp Ser Glu
                165                 170                 175

Glu Asp Asp Met Ser Asp Gly Leu Pro Phe Leu Lys Thr Asp Pro Asn
            180                 185                 190

Asn Asn Gly Phe Phe Gly Asp Gly Ser Leu Leu Cys Ile Leu Arg Ser
        195                 200                 205

Ile Gly Phe Lys Pro Glu Asn Tyr Thr Asn Ser Asn Val Asn Arg Leu
    210                 215                 220

Pro Thr Met Ile Thr Asp Arg Tyr Thr Leu Ala Ser Arg Ser Thr Thr
225                 230                 235                 240

Ser Arg Leu Leu Gln Ser Tyr Leu Asn Asn Phe His Pro Tyr Cys Pro
                245                 250                 255

Ile Val His Ser Pro Thr Leu Met Met Leu Tyr Asn Asn Gln Ile Glu
            260                 265                 270

Ile Ala Ser Lys Asp Gln Trp Gln Ile Leu Phe Asn Cys Ile Leu Ala
        275                 280                 285

Ile Gly Ala Trp Cys Ile Glu Gly Glu Ser Thr Asp Ile Asp Val Phe
    290                 295                 300

Tyr Tyr Gln Asn Ala Lys Ser His Leu Thr Ser Lys Val Phe Glu Ser
305                 310                 315                 320

Gly Ser Ile Ile Leu Val Thr Ala Leu His Leu Leu Ser Arg Tyr Thr
                325                 330                 335
```

-continued

```
Gln Trp Arg Gln Lys Thr Asn Thr Ser Tyr Asn Phe His Ser Phe Ser
            340                 345                 350
Ile Arg Met Ala Ile Ser Leu Gly Leu Asn Arg Asp Leu Pro Ser Ser
            355                 360                 365
Phe Ser Asp Ser Ser Ile Leu Glu Gln Arg Arg Ile Trp Trp Ser
    370                 375                 380
Val Tyr Ser Trp Glu Ile Gln Leu Ser Leu Leu Tyr Gly Arg Ser Ile
385                 390                 395                 400
Gln Leu Ser Gln Asn Thr Ile Ser Phe Pro Ser Ser Val Asp Asp Val
                405                 410                 415
Gln Arg Thr Thr Thr Gly Pro Thr Ile Tyr His Gly Ile Ile Glu Thr
            420                 425                 430
Ala Arg Leu Leu Gln Val Phe Thr Lys Ile Tyr Glu Leu Asp Lys Thr
            435                 440                 445
Val Thr Ala Glu Lys Ser Pro Ile Cys Ala Lys Lys Cys Leu Met Ile
            450                 455                 460
Cys Asn Glu Ile Glu Glu Val Ser Arg Gln Ala Pro Lys Phe Leu Gln
465                 470                 475                 480
Met Asp Ile Ser Thr Thr Ala Leu Thr Asn Leu Leu Lys Glu His Pro
                485                 490                 495
Trp Leu Ser Phe Thr Arg Phe Glu Leu Lys Trp Lys Gln Leu Ser Leu
            500                 505                 510
Ile Ile Tyr Val Leu Arg Asp Phe Phe Thr Asn Phe Thr Gln Lys Lys
            515                 520                 525
Ser Gln Leu Glu Gln Asp Gln Asn Asp His Gln Ser Tyr Glu Val Lys
            530                 535                 540
Arg Cys Ser Ile Met Leu Ser Asp Ala Ala Gln Arg Thr Val Met Ser
545                 550                 555                 560
Val Ser Ser Tyr Met Asp Asn His Asn Val Thr Pro Tyr Phe Ala Trp
                565                 570                 575
Asn Cys Ser Tyr Tyr Leu Phe Asn Ala Val Leu Val Pro Ile Lys Thr
            580                 585                 590
Leu Leu Ser Asn Ser Lys Ser Asn Ala Glu Asn Asn Glu Thr Ala Gln
            595                 600                 605
Leu Leu Gln Gln Ile Asn Thr Val Leu Met Leu Leu Lys Lys Leu Ala
            610                 615                 620
Thr Phe Lys Ile Gln Thr Cys Glu Lys Tyr Ile Gln Val Leu Glu Glu
625                 630                 635                 640
Val Cys Ala Pro Phe Leu Leu Ser Gln Cys Ala Ile Pro Leu Pro His
                645                 650                 655
Ile Ser Tyr Asn Asn Ser Asn Gly Ser Ala Ile Lys Asn Ile Val Gly
            660                 665                 670
Ser Ala Thr Ile Ala Gln Tyr Pro Thr Leu Pro Glu Glu Asn Val Asn
            675                 680                 685
Asn Ile Ser Val Lys Tyr Val Ser Pro Gly Ser Val Gly Pro Ser Pro
            690                 695                 700
Val Pro Leu Lys Ser Gly Ala Ser Phe Ser Asp Leu Val Lys Leu Leu
705                 710                 715                 720
Ser Asn Arg Pro Pro Ser Arg Asn Ser Pro Val Thr Ile Pro Arg Ser
                725                 730                 735
Thr Pro Ser His Arg Ser Val Thr Pro Phe Leu Gly Gln Gln Gln Gln
                740                 745                 750
```

-continued

```
Leu Gln Ser Leu Val Pro Leu Thr Pro Ser Ala Leu Phe Gly Gly Ala
        755                 760                 765

Asn Phe Asn Gln Ser Gly Asn Ile Ala Asp Ser Ser Leu Ser Phe Thr
    770                 775                 780

Phe Thr Asn Ser Ser Asn Gly Pro Asn Leu Ile Thr Thr Gln Thr Asn
785                 790                 795                 800

Ser Gln Ala Leu Ser Gln Pro Ile Ala Ser Ser Asn Val His Asp Asn
            805                 810                 815

Phe Met Asn Asn Glu Ile Thr Ala Ser Lys Ile Asp Asp Gly Asn Asn
        820                 825                 830

Ser Lys Pro Leu Ser Pro Gly Trp Thr Asp Gln Thr Ala Tyr Asn Ala
            835                 840                 845

Phe Gly Ile Thr Thr Gly Met Phe Asn Thr Thr Met Asp Asp Val
        850                 855                 860

Tyr Asn Tyr Leu Phe Asp Asp Glu Asp Thr Pro Pro Asn Pro Lys Lys
865                 870                 875                 880

Glu
```

<210> SEQ ID NO 8
<211> LENGTH: 781
<212> TYPE: DNA
<213> ORGANISM: Schistosoma bovis
<220> FEATURE:
<221> NAME/KEY: CDS
<222> LOCATION: (6)...(641)
<223> OTHER INFORMATION: GST

<400> SEQUENCE: 8

```
atacg atg act ggt gat cac atc aag gtt ata tat ttt aac gga cgc gga        50
      Met Thr Gly Asp His Ile Lys Val Ile Tyr Phe Asn Gly Arg Gly
      1               5                   10                  15 cga gct gaa tcg atc cgg atg aca ctt gtg gca gct ggt gtg aac tac         98
Arg Ala Glu Ser Ile Arg Met Thr Leu Val Ala Ala Gly Val Asn Tyr
                20                  25                  30 gaa gat gag aga att agt ttc caa gat tgg ccg aaa atc aaa cca act        146
Glu Asp Glu Arg Ile Ser Phe Gln Asp Trp Pro Lys Ile Lys Pro Thr
        35                  40                  45 att ccg ggc gga cga ttg cct gca gtg aaa atc acc gat aat cat ggg        194
Ile Pro Gly Gly Arg Leu Pro Ala Val Lys Ile Thr Asp Asn His Gly
    50                  55                  60 cac gtg aaa tgg atg tta gag agt ttg gct att gca cgg tat atg gcg        242
His Val Lys Trp Met Leu Glu Ser Leu Ala Ile Ala Arg Tyr Met Ala
65                  70                  75 aag aag cat cat atg atg gga gaa aca gac gag gag tat tat aat gtt        290
Lys Lys His His Met Met Gly Glu Thr Asp Glu Glu Tyr Tyr Asn Val
    80                  85                  90                  95 gag aag ttg att ggt cag gtt gaa gat cta gaa cat gaa tat cac aaa        338
Glu Lys Leu Ile Gly Gln Val Glu Asp Leu Glu His Glu Tyr His Lys
            100                 105                 110 act ttg atg aag cca gaa gaa gag aaa cag aag ata acc aaa gag ata        386
Thr Leu Met Lys Pro Glu Glu Glu Lys Gln Lys Ile Thr Lys Glu Ile
        115                 120                 125 ctg aac ggc aaa gtg cca gtt ctt ctc gat att atc tgc gaa tct ctg        434
Leu Asn Gly Lys Val Pro Val Leu Leu Asp Ile Ile Cys Glu Ser Leu
    130                 135                 140 aaa gcg tcc aca ggc aag ctg gct gtt ggg gat aaa gtg act cta gcc        482
Lys Ala Ser Thr Gly Lys Leu Ala Val Gly Asp Lys Val Thr Leu Ala
145                 150                 155 gac tta gtt ctg att gct gtc att gac cat gtg act gat ctg gat aaa        530
```

```
Asp Leu Val Leu Ile Ala Val Ile Asp His Val Thr Asp Leu Asp Lys
160                 165                 170                 175 gaa ttt cta act ggc aag tat cct gag atc cat aaa cat aga gaa aat       578
Glu Phe Leu Thr Gly Lys Tyr Pro Glu Ile His Lys His Arg Glu Asn
                180                 185                 190 cta tta gcc agt tca ccg aga ttg gcg aaa tat tta tca gac agg gct       626
Leu Leu Ala Ser Ser Pro Arg Leu Ala Lys Tyr Leu Ser Asp Arg Ala
            195                 200                 205 gca act ccc ttc tag aactgtcaac agaatgctgg gtgtgacgag attgaagata       681
Ala Thr Pro Phe *
        210 ttgatagtag tgcactggtg tgaccttttt acaaagacgt catttgtttt atggtatttt    741 ttttcgcaat cgttattaaa ataaacttag ttttctgttt                          781

<210> SEQ ID NO 9
<211> LENGTH: 211
<212> TYPE: PRT
<213> ORGANISM: Schistosoma bovis

<400> SEQUENCE: 9

Met Thr Gly Asp His Ile Lys Val Ile Tyr Phe Asn Gly Arg Gly Arg
1               5                   10                  15

Ala Glu Ser Ile Arg Met Thr Leu Val Ala Ala Gly Val Asn Tyr Glu
            20                  25                  30

Asp Glu Arg Ile Ser Phe Gln Asp Trp Pro Lys Ile Lys Pro Thr Ile
        35                  40                  45

Pro Gly Gly Arg Leu Pro Ala Val Lys Ile Thr Asp Asn His Gly His
    50                  55                  60

Val Lys Trp Met Leu Glu Ser Leu Ala Ile Ala Arg Tyr Met Ala Lys
65                  70                  75                  80

Lys His His Met Met Gly Glu Thr Asp Glu Glu Tyr Tyr Asn Val Glu
                85                  90                  95

Lys Leu Ile Gly Gln Val Glu Asp Leu Glu His Glu Tyr His Lys Thr
            100                 105                 110

Leu Met Lys Pro Glu Glu Glu Lys Gln Lys Ile Thr Lys Glu Ile Leu
        115                 120                 125

Asn Gly Lys Val Pro Val Leu Leu Asp Ile Ile Cys Glu Ser Leu Lys
    130                 135                 140

Ala Ser Thr Gly Lys Leu Ala Val Gly Asp Lys Val Thr Leu Ala Asp
145                 150                 155                 160

Leu Val Leu Ile Ala Val Ile Asp His Val Thr Asp Leu Asp Lys Glu
                165                 170                 175

Phe Leu Thr Gly Lys Tyr Pro Glu Ile His Lys His Arg Glu Asn Leu
            180                 185                 190

Leu Ala Ser Ser Pro Arg Leu Ala Lys Tyr Leu Ser Asp Arg Ala Ala
        195                 200                 205

Thr Pro Phe
    210

<210> SEQ ID NO 10
<211> LENGTH: 8
<212> TYPE: PRT
<213> ORGANISM: Artificial Sequence
<220> FEATURE:
<223> OTHER INFORMATION: 1X peptide

<400> SEQUENCE: 10
```

-continued

```
Asp Phe Asp Leu Asp Met Leu Gly
  1               5
```

<210> SEQ ID NO 11
<211> LENGTH: 16
<212> TYPE: PRT
<213> ORGANISM: Artificial Sequence
<220> FEATURE:
<223> OTHER INFORMATION: 2X peptide

<400> SEQUENCE: 11

```
Asp Phe Asp Leu Asp Met Leu Gly Asp Phe Asp Leu Asp Met Leu Gly
  1               5                  10                  15
```

<210> SEQ ID NO 12
<211> LENGTH: 32
<212> TYPE: PRT
<213> ORGANISM: Artificial Sequence
<220> FEATURE:
<223> OTHER INFORMATION: 4X peptide

<400> SEQUENCE: 12

```
Asp Phe Asp Leu Asp Met Leu Gly Asp Phe Asp Leu Asp Met Leu Gly
  1               5                  10                  15

Asp Phe Asp Leu Asp Met Leu Gly Asp Phe Asp Leu Asp Met Leu Gly
                 20                  25                  30
```

<210> SEQ ID NO 13
<211> LENGTH: 227
<212> TYPE: PRT
<213> ORGANISM: Artificial Sequence
<220> FEATURE:
<223> OTHER INFORMATION: GST-2X

<400> SEQUENCE: 13

```
Met Thr Gly Asp His Ile Lys Val Ile Tyr Phe Asn Gly Arg Gly Arg
  1               5                  10                  15

Ala Glu Ser Ile Arg Met Thr Leu Val Ala Ala Gly Val Asn Tyr Glu
                 20                  25                  30

Asp Glu Arg Ile Ser Phe Gln Asp Trp Pro Lys Ile Lys Pro Thr Ile
             35                  40                  45

Pro Gly Gly Arg Leu Pro Ala Val Lys Ile Thr Asp Asn His Gly His
         50                  55                  60

Val Lys Trp Met Leu Glu Ser Leu Ala Ile Ala Arg Tyr Met Ala Lys
 65                  70                  75                  80

Lys His His Met Met Gly Glu Thr Asp Glu Glu Tyr Tyr Asn Val Glu
                 85                  90                  95

Lys Leu Ile Gly Gln Val Glu Asp Leu Glu His Glu Tyr His Lys Thr
            100                 105                 110

Leu Met Lys Pro Glu Glu Glu Lys Gln Lys Ile Thr Lys Glu Ile Leu
            115                 120                 125

Asn Gly Lys Val Pro Val Leu Leu Asp Ile Ile Cys Glu Ser Leu Lys
        130                 135                 140

Ala Ser Thr Gly Lys Leu Ala Val Gly Asp Lys Val Thr Leu Ala Asp
145                 150                 155                 160

Leu Val Leu Ile Ala Val Ile Asp His Val Thr Asp Leu Asp Lys Glu
                165                 170                 175

Phe Leu Thr Gly Lys Tyr Pro Glu Ile His Lys His Arg Glu Asn Leu
            180                 185                 190

Leu Ala Ser Ser Pro Arg Leu Ala Lys Tyr Leu Ser Asp Arg Ala Ala
```

-continued

```
              195                 200                 205
Thr Pro Phe Asp Phe Asp Leu Asp Met Leu Gly Asp Phe Asp Leu Asp
    210                 215                 220

Met Leu Gly
225
```

<210> SEQ ID NO 14
<211> LENGTH: 243
<212> TYPE: PRT
<213> ORGANISM: Artificial Sequence
<220> FEATURE:
<223> OTHER INFORMATION: GST-4X

<400> SEQUENCE: 14

```
Met Thr Gly Asp His Ile Lys Val Ile Tyr Phe Asn Gly Arg Gly Arg
1               5                   10                  15

Ala Glu Ser Ile Arg Met Thr Leu Val Ala Ala Gly Val Asn Tyr Glu
            20                  25                  30

Asp Glu Arg Ile Ser Phe Gln Asp Trp Pro Lys Ile Lys Pro Thr Ile
        35                  40                  45

Pro Gly Gly Arg Leu Pro Ala Val Lys Ile Thr Asp Asn His Gly His
    50                  55                  60

Val Lys Trp Met Leu Glu Ser Leu Ala Ile Ala Arg Tyr Met Ala Lys
65                  70                  75                  80

Lys His His Met Met Gly Glu Thr Asp Glu Glu Tyr Tyr Asn Val Glu
                85                  90                  95

Lys Leu Ile Gly Gln Val Glu Asp Leu Glu His Glu Tyr His Lys Thr
            100                 105                 110

Leu Met Lys Pro Glu Glu Glu Lys Gln Lys Ile Thr Lys Glu Ile Leu
        115                 120                 125

Asn Gly Lys Val Pro Val Leu Leu Asp Ile Ile Cys Glu Ser Leu Lys
    130                 135                 140

Ala Ser Thr Gly Lys Leu Ala Val Gly Asp Lys Val Thr Leu Ala Asp
145                 150                 155                 160

Leu Val Leu Ile Ala Val Ile Asp His Val Thr Asp Leu Asp Lys Glu
                165                 170                 175

Phe Leu Thr Gly Lys Tyr Pro Glu Ile His Lys His Arg Glu Asn Leu
            180                 185                 190

Leu Ala Ser Ser Pro Arg Leu Ala Lys Tyr Leu Ser Asp Arg Ala Ala
        195                 200                 205

Thr Pro Phe Asp Phe Asp Leu Asp Met Leu Gly Asp Phe Asp Leu Asp
    210                 215                 220

Met Leu Gly Asp Phe Asp Leu Asp Met Leu Gly Asp Phe Asp Leu Asp
225                 230                 235                 240

Met Leu Gly
```

<210> SEQ ID NO 15
<211> LENGTH: 345
<212> TYPE: PRT
<213> ORGANISM: Artificial Sequence
<220> FEATURE:
<223> OTHER INFORMATION: His-tag-hTBP

<400> SEQUENCE: 15

```
His His His His His His Met Asp Gln Asn Asn Ser Leu Pro Pro Tyr
1               5                   10                  15

Ala Gln Gly Leu Ala Ser Pro Gln Gly Ala Met Thr Pro Gly Ile Pro
```

```
            20                  25                  30
Ile Phe Ser Pro Met Met Pro Tyr Gly Thr Gly Leu Thr Pro Gln Pro
         35                  40                  45

Ile Gln Asn Thr Asn Ser Leu Ser Ile Leu Glu Glu Gln Gln Arg Gln
     50                  55                  60

Gln Gln Gln Gln Gln Gln Gln Gln Gln Gln Gln Gln Gln Gln Gln Gln
 65                  70                  75                  80

Gln Gln Gln Gln Gln Gln Gln Gln Gln Gln Gln Gln Gln Gln Gln Gln
                 85                  90                  95

Gln Gln Gln Gln Gln Ala Val Ala Ala Ala Val Gln Gln Ser Thr
                100                 105                 110

Ser Gln Gln Ala Thr Gln Gly Thr Ser Gly Gln Ala Pro Gln Leu Phe
            115                 120                 125

His Ser Gln Thr Leu Thr Thr Ala Pro Leu Pro Gly Thr Thr Pro Leu
    130                 135                 140

Tyr Pro Ser Pro Met Thr Pro Met Thr Pro Ile Thr Pro Ala Thr Pro
145                 150                 155                 160

Ala Ser Glu Ser Ser Gly Ile Val Pro Gln Leu Gln Asn Ile Val Ser
                165                 170                 175

Thr Val Asn Leu Gly Cys Lys Leu Asp Leu Lys Thr Ile Ala Leu Arg
            180                 185                 190

Ala Arg Asn Ala Glu Tyr Asn Pro Lys Arg Phe Ala Ala Val Ile Met
        195                 200                 205

Arg Ile Arg Glu Pro Arg Thr Thr Ala Leu Ile Phe Ser Ser Gly Lys
    210                 215                 220

Met Val Cys Thr Gly Ala Lys Ser Glu Glu Gln Ser Arg Leu Ala Ala
225                 230                 235                 240

Arg Lys Tyr Ala Arg Val Val Gln Lys Leu Gly Phe Pro Ala Lys Phe
                245                 250                 255

Leu Asp Phe Lys Ile Gln Asn Met Val Gly Ser Cys Asp Val Lys Phe
            260                 265                 270

Pro Ile Arg Leu Glu Gly Leu Val Leu Thr His Gln Gln Phe Ser Ser
        275                 280                 285

Tyr Glu Pro Glu Leu Phe Pro Gly Leu Ile Tyr Arg Met Ile Lys Pro
    290                 295                 300

Arg Ile Val Leu Leu Ile Phe Val Ser Gly Lys Val Val Leu Thr Gly
305                 310                 315                 320

Ala Lys Val Arg Ala Glu Ile Tyr Glu Ala Phe Glu Asn Ile Tyr Pro
                325                 330                 335

Ile Leu Lys Gly Phe Arg Lys Thr Thr
            340                 345

<210> SEQ ID NO 16
<211> LENGTH: 233
<212> TYPE: PRT
<213> ORGANISM: Artificial Sequence
<220> FEATURE:
<223> OTHER INFORMATION: His-tag-GST-2X

<400> SEQUENCE: 16

His His His His His His Met Thr Gly Asp His Ile Lys Val Ile Tyr
 1               5                  10                  15

Phe Asn Gly Arg Gly Arg Ala Glu Ser Ile Arg Met Thr Leu Val Ala
                20                  25                  30

Ala Gly Val Asn Tyr Glu Asp Glu Arg Ile Ser Phe Gln Asp Trp Pro
```

-continued

```
                35                  40                  45
Lys Ile Lys Pro Thr Ile Pro Gly Gly Arg Leu Pro Ala Val Lys Ile
 50                  55                  60

Thr Asp Asn His Gly His Val Lys Trp Met Leu Glu Ser Leu Ala Ile
 65                  70                  75                  80

Ala Arg Tyr Met Ala Lys Lys His His Met Met Gly Glu Thr Asp Glu
                 85                  90                  95

Glu Tyr Tyr Asn Val Glu Lys Leu Ile Gly Gln Val Glu Asp Leu Glu
                100                 105                 110

His Glu Tyr His Lys Thr Leu Met Lys Pro Glu Glu Glu Lys Gln Lys
            115                 120                 125

Ile Thr Lys Glu Ile Leu Asn Gly Lys Val Pro Val Leu Leu Asp Ile
        130                 135                 140

Ile Cys Glu Ser Leu Lys Ala Ser Thr Gly Lys Leu Ala Val Gly Asp
145                 150                 155                 160

Lys Val Thr Leu Ala Asp Leu Val Leu Ile Ala Val Ile Asp His Val
                165                 170                 175

Thr Asp Leu Asp Lys Glu Phe Leu Thr Gly Lys Tyr Pro Glu Ile His
            180                 185                 190

Lys His Arg Glu Asn Leu Leu Ala Ser Ser Pro Arg Leu Ala Lys Tyr
        195                 200                 205

Leu Ser Asp Arg Ala Ala Thr Pro Phe Asp Phe Asp Leu Asp Met Leu
    210                 215                 220

Gly Asp Phe Asp Leu Asp Met Leu Gly
225                 230

<210> SEQ ID NO 17
<211> LENGTH: 249
<212> TYPE: PRT
<213> ORGANISM: Artificial Sequence
<220> FEATURE:
<223> OTHER INFORMATION: His-tag-GST-4X

<400> SEQUENCE: 17

His His His His His His Met Thr Gly Asp His Ile Lys Val Ile Tyr
  1               5                  10                  15

Phe Asn Gly Arg Gly Arg Ala Glu Ser Ile Arg Met Thr Leu Val Ala
                 20                  25                  30

Ala Gly Val Asn Tyr Glu Asp Glu Arg Ile Ser Phe Gln Asp Trp Pro
             35                  40                  45

Lys Ile Lys Pro Thr Ile Pro Gly Gly Arg Leu Pro Ala Val Lys Ile
 50                  55                  60

Thr Asp Asn His Gly His Val Lys Trp Met Leu Glu Ser Leu Ala Ile
 65                  70                  75                  80

Ala Arg Tyr Met Ala Lys Lys His His Met Met Gly Glu Thr Asp Glu
                 85                  90                  95

Glu Tyr Tyr Asn Val Glu Lys Leu Ile Gly Gln Val Glu Asp Leu Glu
                100                 105                 110

His Glu Tyr His Lys Thr Leu Met Lys Pro Glu Glu Glu Lys Gln Lys
            115                 120                 125

Ile Thr Lys Glu Ile Leu Asn Gly Lys Val Pro Val Leu Leu Asp Ile
        130                 135                 140

Ile Cys Glu Ser Leu Lys Ala Ser Thr Gly Lys Leu Ala Val Gly Asp
145                 150                 155                 160

Lys Val Thr Leu Ala Asp Leu Val Leu Ile Ala Val Ile Asp His Val
```

-continued

```
                165                 170                 175
Thr Asp Leu Asp Lys Glu Phe Leu Thr Gly Lys Tyr Pro Glu Ile His
                180                 185                 190

Lys His Arg Glu Asn Leu Leu Ala Ser Ser Pro Arg Leu Ala Lys Tyr
            195                 200                 205

Leu Ser Asp Arg Ala Ala Thr Pro Phe Asp Phe Asp Leu Asp Met Leu
        210                 215                 220

Gly Asp Phe Asp Leu Asp Met Leu Gly Asp Phe Asp Leu Asp Met Leu
225                 230                 235                 240

Gly Asp Phe Asp Leu Asp Met Leu Gly
                245

<210> SEQ ID NO 18
<211> LENGTH: 15
<212> TYPE: PRT
<213> ORGANISM: Artificial Sequence
<220> FEATURE:
<223> OTHER INFORMATION: linker

<400> SEQUENCE: 18

Ser Ser Ser Ser Gly Ser Ser Ser Gly Ser Ser Ser Gly
1               5                   10                  15

<210> SEQ ID NO 19
<211> LENGTH: 31
<212> TYPE: PRT
<213> ORGANISM: Artificial Sequence
<220> FEATURE:
<223> OTHER INFORMATION: 1X-linker-1X

<400> SEQUENCE: 19

Asp Phe Asp Leu Asp Met Leu Gly Ser Ser Ser Gly Ser Ser Ser
1               5                   10                  15

Ser Gly Ser Ser Ser Gly Asp Phe Asp Leu Asp Met Leu Gly
            20                  25                  30

<210> SEQ ID NO 20
<211> LENGTH: 231
<212> TYPE: PRT
<213> ORGANISM: Artificial Sequence
<220> FEATURE:
<223> OTHER INFORMATION: His-tag-GAL4-VP16

<400> SEQUENCE: 20

His His His His His Met Lys Leu Leu Ser Ser Ile Glu Gln Ala
1               5                   10                  15

Cys Asp Ile Cys Arg Leu Lys Lys Leu Lys Cys Ser Lys Glu Lys Pro
            20                  25                  30

Lys Cys Ala Lys Cys Leu Lys Asn Asn Trp Glu Cys Arg Tyr Ser Pro
        35                  40                  45

Lys Thr Lys Arg Ser Pro Leu Thr Arg Ala His Leu Thr Glu Val Glu
    50                  55                  60

Ser Arg Leu Glu Arg Leu Glu Gln Leu Phe Leu Leu Ile Phe Pro Arg
65                  70                  75                  80

Glu Asp Leu Asp Met Ile Leu Lys Met Asp Ser Leu Gln Asp Ile Lys
                85                  90                  95

Ala Leu Leu Thr Gly Leu Phe Val Gln Asp Asn Val Asn Lys Asp Ala
            100                 105                 110

Val Thr Asp Arg Leu Ala Ser Val Glu Thr Asp Met Pro Leu Thr Leu
        115                 120                 125
```

-continued

```
Arg Gln His Arg Ile Ser Ala Thr Ser Ser Ser Glu Glu Ser Ser Asn
    130                 135                 140

Lys Gly Gln Arg Gln Leu Thr Val Ser Thr Ala Pro Ile Thr Asp Val
145                 150                 155                 160

Ser Leu Gly Asp Glu Leu Arg Leu Asp Gly Glu Glu Val Asp Met Thr
                165                 170                 175

Pro Ala Asp Ala Leu Asp Asp Phe Asp Leu Glu Met Leu Gly Asp Val
            180                 185                 190

Glu Ser Pro Ser Pro Gly Met Thr His Asp Pro Val Ser Tyr Gly Ala
        195                 200                 205

Leu Asp Val Asp Asp Phe Glu Phe Glu Gln Met Phe Thr Asp Ala Met
    210                 215                 220

Gly Ile Asp Asp Phe Gly Gly
225                 230
```

USE OF SELF-ASSEMBLED MONOLAYERS TO PROBE THE STRUCTURE OF A TARGET MOLECULE

This application claims priority from provisional patent application 60/087,766 filed on Jun. 2, 1998.

STATEMENT AS TO RIGHTS TO INVENTIONS MADE UNDER FEDERALLY SPONSORED RESEARCH AND DEVELOPMENT

This work was supported, in part, by NIH Grants 5T32EM-07598-18 and GM-32308. The government of the United States of America may have some rights in this invention.

FIELD OF INVENTION

The present invention relates to the use of self-assembled monolayers attached to surfaces for the detection and probing of target molecule structure and function.

BACKGROUND OF THE INVENTION

Combinatorial chemistry techniques are used to synthesize diverse "libraries" of unique chemical compounds. These small molecule libraries often yield drug candidates that are capable of binding a specific biological target but because of their small size and relative simple chemical makeup, they characteristically interact with the target in a low affinity interaction. These low affinity interactions cannot adequately compete with larger more diverse natural ligands, like proteins and protein complexes, and thus provide little therapeutic value. Natural products, which are naturally occurring organisms isolated from soils, yeast, marine organisms, and the like are larger and chemically more interesting than small molecules from combinatorial libraries. Natural products are routinely screened for therapeutic activity against disease-related organisms. Many cancer drugs have been identified in this way. The problem with developing a natural product for the drug market is that they are large and chemically complicated, which means that elaborate and expensive schemes for their synthesis must be developed. Identifying a synthetic scheme that is commercially feasible is a technical challenge that at best takes years and millions of dollars to accomplish and at worst cannot be done. For this reason, there is interest in enhancing the affinity between small molecule drugs and their biologically relevant targets.

Knowles and colleagues, at Harvard, reported that they could enhance the binding affinity of a small molecule for a particular target by attaching a "greasy tail" to the small molecule. This hydrophobic tail was later shown to interact with a hydrophobic patch on the target molecule adjacent to the binding site.

Many biologically relevant target molecules present more than one binding site for a particular ligand. Some present pseudo identical binding sites with which they bind natural ligands that contain "repeats" of a binding motif. It is known that bivalent interactions (like antibody interactions) are higher affinity interactions than monovalent interactions, due to the cooperative binding effect. Therefore, one would like to link several small molecule drugs together to form a pseudo multivalent drug that would interact more strongly with a multi-binding-site target molecule. The problem with this logic is that the enthalpic advantage of the additional binding energy is offset by the large entropic energy cost of ordering the connected binding moieties. However, making the linker between the binding moieties a rigid linker would introduce order and thus minimize the entropic cost to yield a higher affinity interaction. In order to connect two binding moieties (the small molecule drugs) with a rigid linker, in a geometry that would encourage its binding to the target molecule, one would need to know apriori the distance between the binding sites on the target molecule. This inter-binding-site distance information is currently derived from X-ray or NMR structure determination of the target molecule. This process is time-consuming (years) and expensive.

The subject of this invention is how (self-assembled monolayers (SAMs) can be used to present discrete binding moieties, at varying densities, in a rigid 2-dimensional array, to multivalent target molecules in order to promote a higher affinity, cooperative interaction. Ligand densities within the SAM are varied to determine the critical distance between binding moieties that will promote simultaneous, cooperative binding of the target molecule. By monitoring the kinetics of binding events between the target molecule and the variable density ligand surfaces, one can empirically determine the lowest surface density that prompts a large shift in affinity for the multivalent target molecule. One can then use Poisson statistics to infer the distance between surface-immobilized ligands and thus also the distance between the binding sites on the target molecule. Once this distance information has been deduced, it can be used to rationally design bi- or multi-valent drugs or rigid-linkers to connect two binding moieties. Alternatively, the SAM itself can become a part of the "drug"; in this case, the SAM is used as the "rigid linker" between binding moieties to present multiple binding motifs, at the empirically determined critical density, to promote the higher affinity cooperative interaction. The SAM, presented ligands and underlying gold (may be gold colloids) are both the drug and the drug delivery system. Inert thiols of the SAMs can be terminated with lipid-like groups to facilitate drug delivery. Similarly, a biospecific ligand could be incorporated (at varying densities) into a liposome, at the critical presentation density determined, and used directly as a multivalent drug in its own delivery system.

SUMMARY OF THE INVENTION

Self-assembled monolayers are used as a rigid 2-dimensional matrix for presenting binding moieties, at varying distances from each other, to a target molecule. Two-component SAMs incorporate an inert spacer molecule and a biospecific molecule that can directly or indirectly present a binding moiety to a target molecule. The distance between the biospecific molecules in the array, the ligand density, is controlled by manipulating the concentrations of the two component thiols in solution before deposition onto gold. The affinity of the interaction between the surface immobilized ligands and the multivalent target molecule is monitored as a function of ligand density. The lowest ligand surface density that elicits a jump in affinity for the target molecule contains the critical information needed to extract the distance between binding sites on the target molecule. The dimensions of the hexagonal tiling pattern formed when the sulfurs from the thiols bind to gold solid are known. Therefore, Poisson statistics can be used to infer the distance between surface immobilized ligands, and thus the inter-binding-site distance on the target molecule, from the concentrations of the thiols in solution. Further, the gold surface itself and the attached SAM can be used as a scaffold to present binding moieties, in a controlled, higher affinity geometry, to a target molecule.

In a preferred embodiment, SAMs are generated that incorporate two thiol types: 1) an inert-tri-ethylene glycol-terminated thiol and 2) a nitrilo tri-acetic acid (NTA) terminated thiol that when complexed with Ni, captures histidine-tagged proteins or peptides. The density of NTA-thiol within the SAM is varied to present varying densities of a histidine-tagged binding moiety to a multi-valent target molecule. The affinity of the interaction is plotted as a function of ligand density within the SAM. A dramatic increase in the binding affinity occurs at a critical surface density when the presented ligands are close enough to each other to simultaneously bind to a common target molecule. The solution concentrations of the two thiol types and the dimensions of the tiling pattern that the thiols form on the gold substrate are input into Poisson distribution equations to extract the probable distance between binding sites on a target molecule.

BRIEF DESCRIPTION OF THE DRAWINGS

FIG. 8 shows that there is a synergistic increase in affinity between hTBPc (SEQ ID NO:3) in solution and surface-bound GST-2X (SEQ ID NO:13) when the density of immobilization is increased from 3.8% to 5.7%.

FIG. 9 shows competitive inhibition experiments demonstrating that 2X (SEQ ID NO:11) ligands behave very differently in solution versus when immobilized.

DETAILED DESCRIPTION OF PREFERRED EMBODIMENTS

Figure 1:
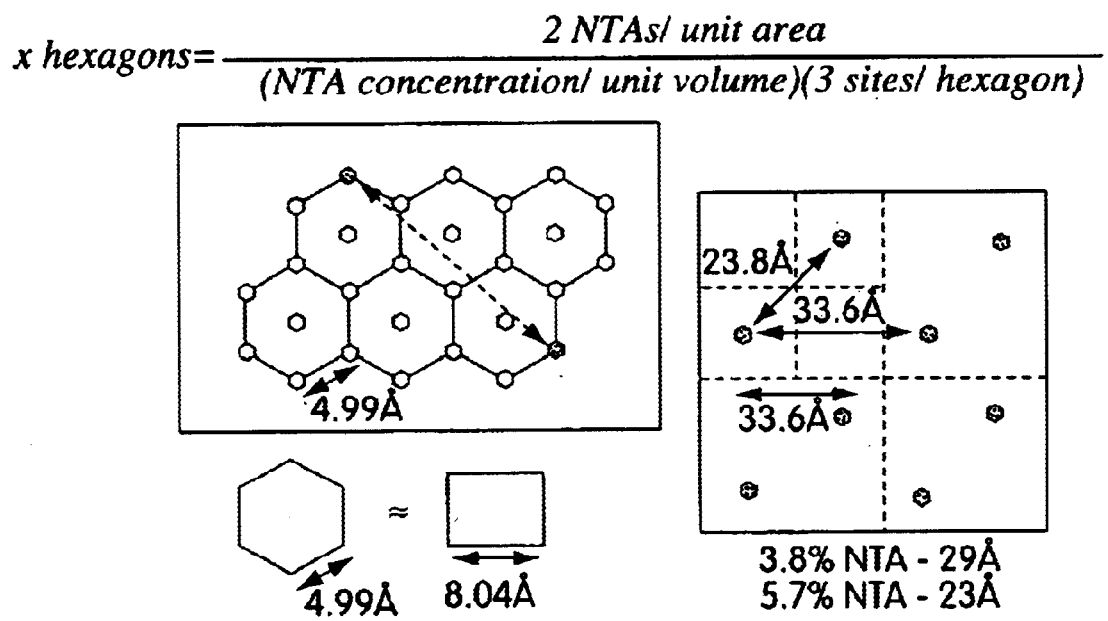
FIG. 1 shows the predicted structure of mixed self-assembled monolayers made by doping a thiol solution with a nitriloacetic acid terminated thiol.

Variable density nitrilotriacetic acid (NTA)-SAMs were used to probe the binding site(s) of a biologically important molecule, the human general transcription factor-TATA box binding protein (hTBP) [Burley, S. K. and Roeder, R. G. (1996) Biochemistry and structural biology of transcription factor IID (TFIID). *Annu. Rev. Biochem.* 65:769–799]. This transcription factor has been implicated as a direct target of transcriptional activators such as VP16 [Ingles, J. C., M. Shales, W. D. Cress, S. J. Triezenberg and J. Greenblatt. (1991) Reduced binding of TFIID to transcriptionally compromised mutants of VP16. *Nature.* 351:588–590]. In fact, the need for,an activator is eliminated when TBP is artificially tethered to a DNA promoter [Xiao, H., J. D. Friesen and J. T. Lis. 1995. Recruiting TATA-binding protein to a promoter: transcriptional activation without an upstream activator. *Mol. and Cell. Biol.* 15(10):5757–5761].

Transcriptional activator proteins are modular in that they have functionally separable domains [Brent, R. and M. Ptashne. (1985) A Eukaryotic transcriptional activator bearing the DNA specificity of a prokaryotic repressor. *Cell.* 43:729–736], a DNA binding domain, and an activating region. The structures of TBP [Nikolov, D. B., H. Chen, E. D. Halay, A. A. Usheva, K. Hisatake, D. K. Lee, R. G. Roeder and S. K. Burley. (1995) Crystal structure of a TFIIB-TBP-TATA element ternary complex. *Nature.* 377:119–128] and several activator DNA binding domains [Marmorstein, R., M. Carey, M. Ptashne, and S. C. Harrison. 1992. DNA recognition by Ga14: structure of a protein/DNA complex. *Nature.* 356:408–414; Ellenberger et al., 1992; and Baleja, J. D., R. Marmorstein, S. C. Harrison and G. Wagner. 1992]. The structure of the DNA-binding domain of Cd2-Gal4 from Saccaromyces cervisiae in solution has been solved, yet the structure of an activating region, alone or complexed with a target molecule has remained elusive. Fundamental questions as to how an activating region effects gene transcription remain unanswered. One mechanistic model of gene activation proposes that DNA-bound activators trigger transcription by merely "recruiting" some necessary factor, perhaps TBP, to the promoter through direct contact with the activating region [Triezenberg, S. J., 1995. Structure and function of activation domains. *Curr. Opin. Genet. Dev.,* 5(2): 190–196]. Another model proposes that activating regions induce a conformational change in a target protein(s) [Sheldon and Reinberg, 1995] or sequentially perform some function until a threshold is reached which catalyzes gene transcription.

In eukaryotes, more than one DNA-tethered activator is typically required to achieve activated transcription and that multiply bound activators transcribe synergistically [Lin, Y. S., M. Carey, M. Ptashne and M. R. Green. (1990) How different eukaryotic transcriptional activators can cooperate promiscuously. *Nature* 345:359–361]. Cryptic repeats of minimal activation motifs have been identified in eukaryotic activators that, when tandemly reiterated and tethered to DNA, efficiently activate transcription in vitro [Blair et al., 1994; Tanaka, M. and W. Herr, (1994) Reconstitution of transcriptional activation domains by reiteration of short peptide segments reveals the modular organization of a glutamine-rich activation domain. *Mol. Cell. Biol.* 14(9): 6056–6067]. An eight amino acid minimal activation motif (DFDLDMLG) (SEQ ID NO:10) derived from the prototypic mammalian activator VP16 was recently identified [Tanaka, M. (1996) Modulation of promoter occupancy by cooperative DNA binding and activation-function is a major determinant of transcriptional regulation by activators in vivo. *Proc. Natl. Acad Sci. USA*. 93(9):4311–4315]. As an exemplary embodiment, this invention describes novel biophysical methods to quantitate the kinetics, as well as investigate the mechanism, of the interaction between hTBP and tandem repeats of the VP 16 minimal motif.

The interactions were characterized by SPR in a BIAcore instrument. SPR is a fairly new optical technique for the real time detection and kinetic analysis of intermolecular interactions [Liedberg, B., C. Nylander and L. Lundstrom. (1983) Surface plasmon resonance for gas detection and biosensing. *Sens. Actuators.* 4(2):299–304; Daniels et al., 1988; Lofas, S. and Johnsson, B. (1990) A novel hydrogel matrix on gold surfaces in surface plasmon resonance sensors for fast and efficient covalent immobilization of ligands. J Chem. Soc., Chem. Commun.: 1526–1528]. The basis of the technology is as follows: ligands are immobilized on a surface; putative target molecules are flowed over this surface; the protein concentration at the solution-surface interface changes as target binds ligand. The increased protein mass at the interface causes a change in the optical properties of the system. The amount of new protein recruited to the interfacial region can be quantitated by measuring the change in the angle at which light reflected off the interface is a minimum [for a review see Bamdad, C. 1997. Surface plasmon resonance for measurements of biological interest. *Current Protocols in Molecular Biology* 20.4.1–20.4.12.]. Changes in this angle are measured in resonance units (RUs) where 1 RU is defined as a change of 1/10,000th of a degree. A rule of thumb is that for a distance of about 150 mn from the interface, 1 ng protein/mm$^2$ registers $10^3$ RUs.

SAMs were generated that incorporated an NTA group for the specific binding of histidine-tagged peptides. The density of NTA in the SAM was varied so that different amounts of a His-tagged activation motif could be presented to TBP, in solution. SPR was used to quantitate avidity effects between TBP and surface-bound peptides as a function of peptide density.

FIG. 1 shows mixed self-assembled monolayers (SAMs) that were generated by doping a thiol solution with an NTA-terminated thiol and designed to capture histidine-tagged proteins. Sulfur atoms deposit on gold substrates in a hexagonal tiling pattern 4.99 Å on edge with three possible positions for thiol deposition per hexagon. If it is assumed that in a well-ordered SAM all sites are occupied, Poisson statistics can be used to calculate an average distance between NTA-thiols for a given NTA concentration. Equation (1) calculates how many hexagons must be filled before two NTA-thiols are deposited. For a 3.8% NTA-thiol concentration in solution, relative to EG$_3$-thiol, an average of 17.5 hexagons must be filled before 2 NTA ligands appear. For a 5.7% NTA solution, 11.7 hexagons must be filled before an average of two NTA ligands are deposited. The area of a hexagon 4.99 Å on edge is 64.69 Å$^2$ which is equal to the area of a square, 8.04 Å on edge. NTA ligands on SAMs formed from a 3.8% NTA-thiol solution would be an average of 29 Å apart, while NTA ligands in a SAM formed from a 5.7% NTA-thiol solution would be 23 Å apart. It was assumed that the concentration of NTA-thiol in solution was equal to its concentration in the SAM; see FIG. 2 of Sigal et al., 1996.

Figure 2:
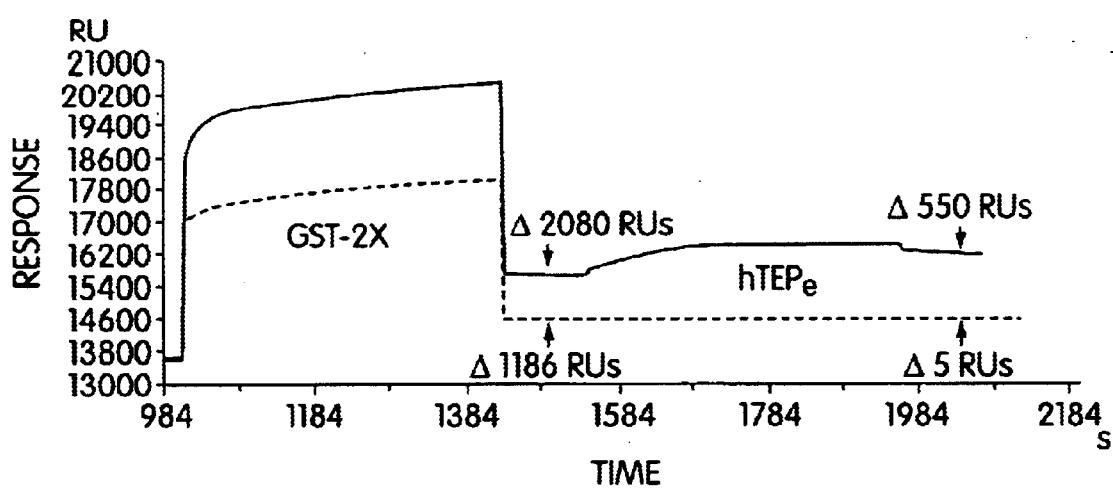
FIG. 2 shows the results of the binding of hTBPc (SEQ ID NO:3) to GST-2X (SEQ ID NO:13) peptide surfaces of differing densities.

FIG. 2 shows that hTBPc in solution will not bind to GST-2X peptide surfaces unless peptides are immobilized close to one another. The BIAcore SPR instrument records changes in the angle of minimum reflectance (RUs) as a function of time. Reagents are flowed over individual flow cells of the SAM. The "square waves" represent injections of protein "plugs" that interrupt the constant buffer flow. An association constant can be derived from an analysis of the initial phase of the injection and a dissociation rate can be extracted from analysis of the system as it returns to buffer flow. GST-2X or $^4$X (SEQ ID NO:12) fusion proteins (X=DFDLDMLG) (SEQ ID NO:3) were separately immobilized on NTA-SAMs via histidine-tags then hTBPc (124 nM) was injected over the surfaces. An overlay of two SPR sensorgrams shows that hTBPc (SEQ ID NO:3) does not bind to GST-2X (SEQ ID NO:13) immobilized on a 3.8% NTA-SAM (dashed line) but binds very tightly when immobilized on a 5.7% NTA-SAM (solid-line).

Figure 3:
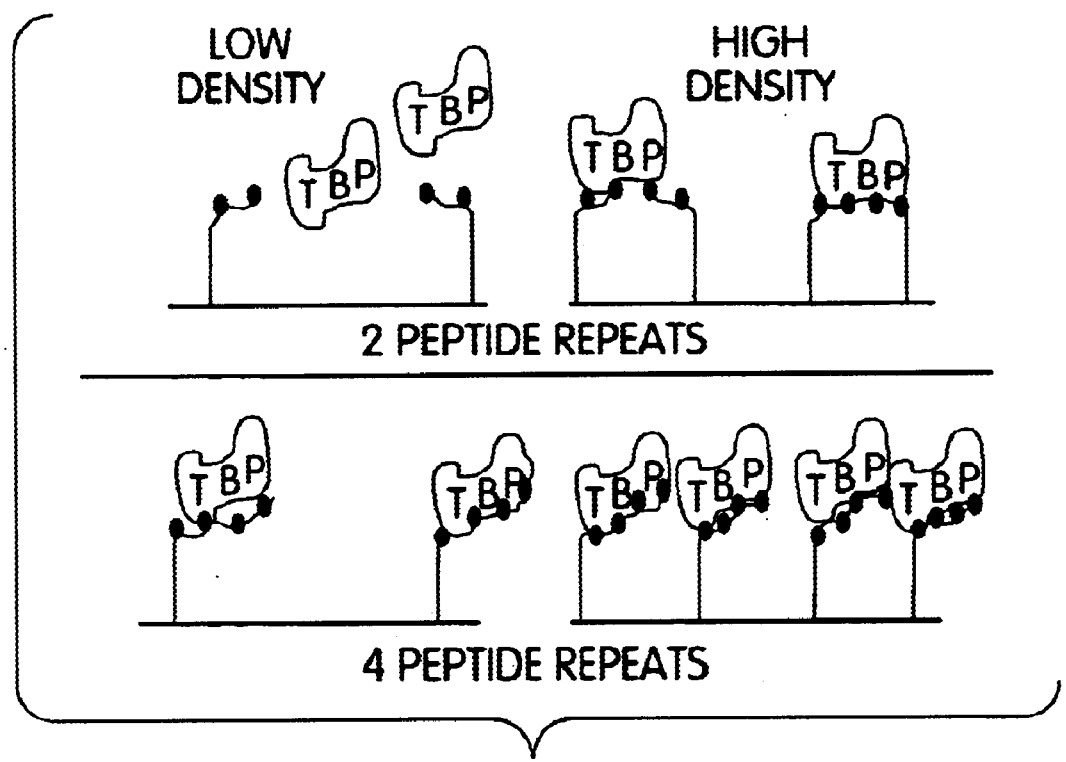
FIG. 3 shows the binding of TBP (SEQ ID NO:2) target protein as a function of peptide surface density.

FIG. 3 shows the binding of target protein TBP measured by SPR as a function of peptide surface density. A series of NTA-SAMs were generated to display peptides at low to high density. When two tandem repeats of the minimal activation peptide (GST2X) (SEQ ID NO:13) were displayed at low density (1.3%–3.8%), human TBPc (SEQ ID NO:3) did not bind to the surface. In contrast, a more dense GST-2X surface (5.7%–11.4%), bound significant amounts of human TBPc. Fusion proteins bearing four tandem repeats of the minimal activation peptide (GST-4X) (SEQ ID NO:14) bound hTBPc whether the peptides were displayed at low or high density. The stoichiometry of the interaction was a constant, independent of the immobilization density. Notably, at corresponding surface concentrations, GST-2X bound half as much hTBPc as GST-4X, suggesting that two-2X modules immobilized at close proximity to each other (high density) simultaneously contact one hTBPc molecule.

Figure 4:
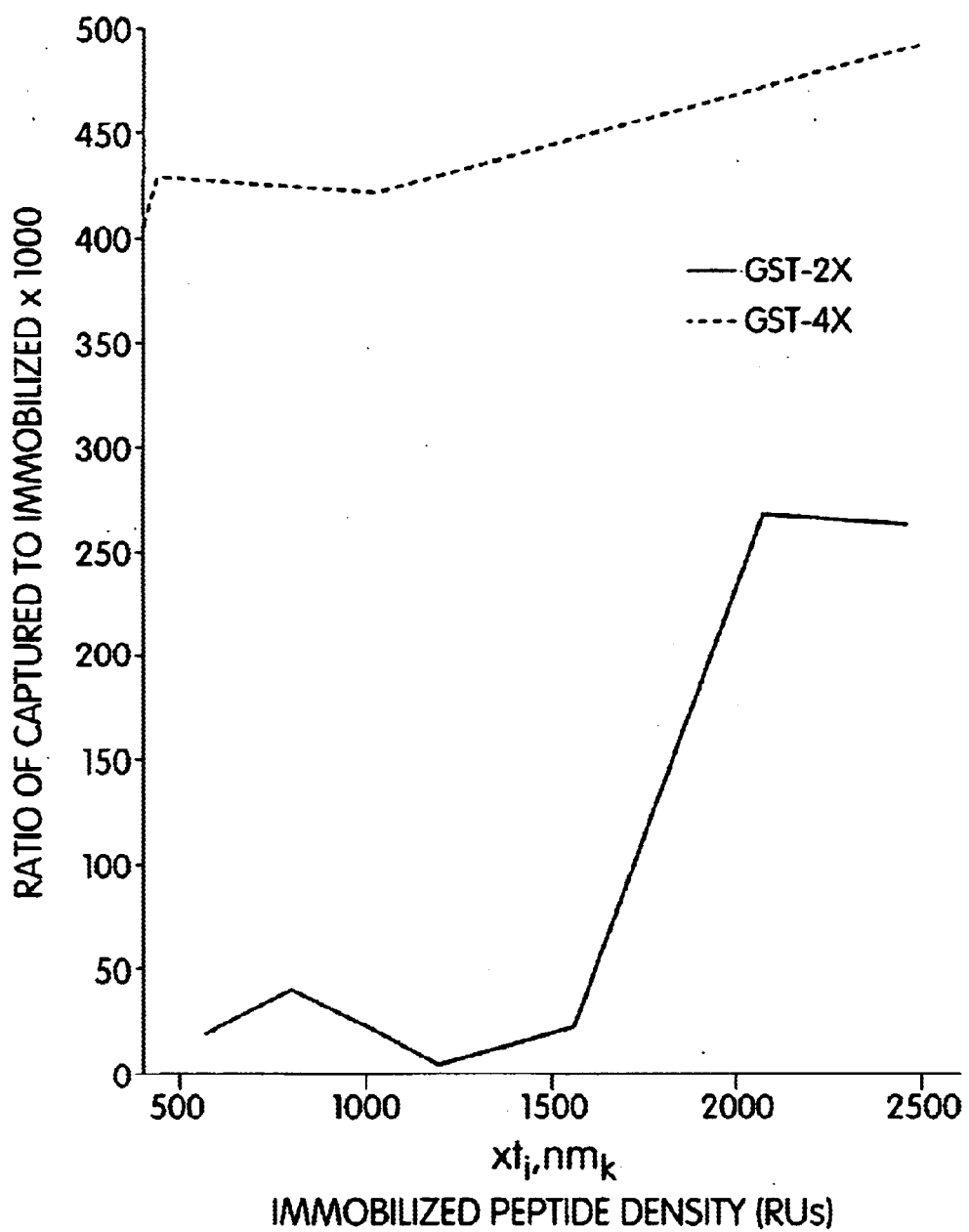
FIG. 4 shows that the binding of hTBPc (SEQ ID NO:3) to surface immobilized GST-2X (SEQ ID NO:13) is a non-linear function of the surface density of the peptide.

FIG. 4 shows that the binding of hTBPc (SEQ ID NO:3) to surface immobilized GST-2X (SEQ ID NO:13) is a non-linear function of the surface density of the peptide. Histidine-tagged peptides were separately immobilized on SAMs presenting NTA over a wide range of surface densities. SPR was used to quantitate the amount of target protein, hTBPc that bound to each surface. The mass ratios of captured hTBPc to surface immobilized peptide (GST-2X or -4X) (SEQ ID NOs:13 or 14) was plotted as a function of peptide concentration. The binding of hTBPc to GST4X (dashed line) is roughly constant over the range of surface peptide densities. However, the binding of hTBPc to GST-2X (solid line) approximates a step function of GST-2X surface concentration.

Figure 5:
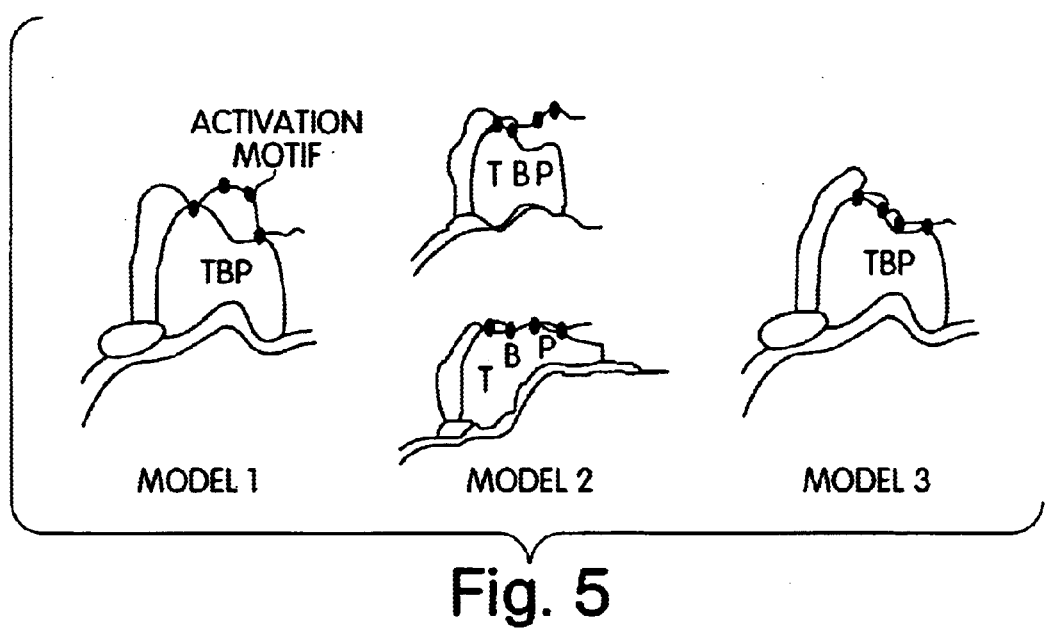
FIG. 5 shows the three possible mechanistic models for describing the interaction of TBP (SEQ ID NO:11) with reiterated peptide activation motifs.

FIG. 5 shows experiments that were designed to discriminate between three possible mechanistic models to explain how reiterated peptide activation motifs synergistically effect transcription of a nearby gene. Model 1: two connected peptide motifs must be positioned such that they can simultaneously bind to quasi-identical sites on TBP (SEQ ID NO:2). The bivalent, high affinity interaction would keep the general transcription factor tethered near the start site of transcription awaiting other steps in the transcriptional activation process. Model 2: the binding of one or two peptide activation motifs causes a conformational change in TBP. The allosteric effect enhances the subsequent binding of additional peptide motifs and a high affinity interaction results. Model 3: a high affinity interaction occurs between the peptide repeats and TBP but rather than resulting from a "bivalent" interaction or an allosteric effect, it results from the simple summation of multiple interactions between TBP and the entire length of the activation peptide.

Figure 6:
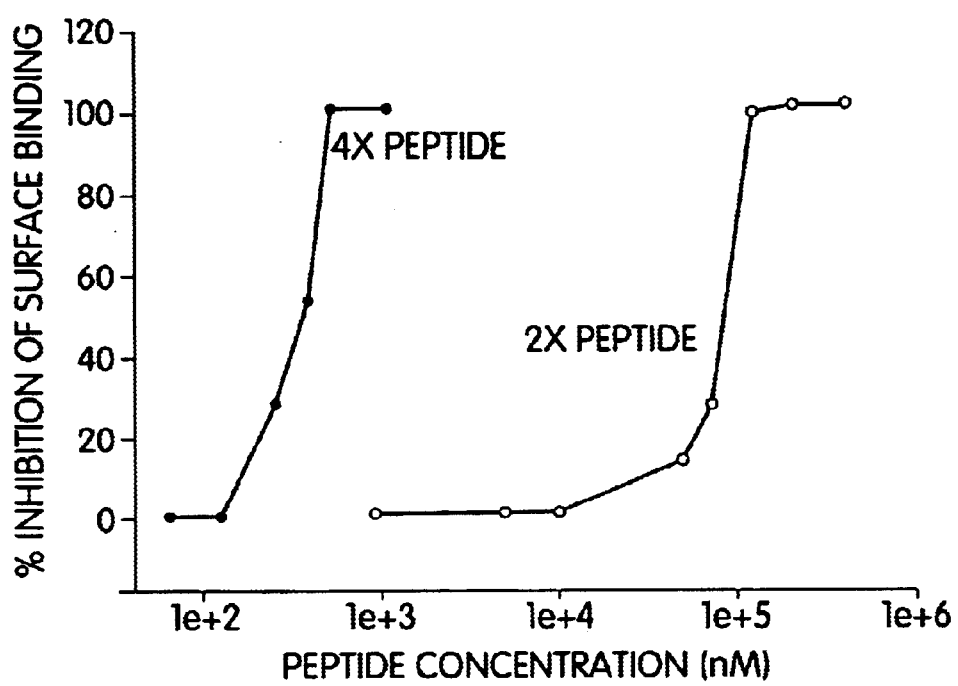
FIG. 6 shows titration curves summarizing competitive inhibition experiments designed to measure the kinetics of hTBPc-peptide activation motif binding.

FIG. 6 shows titration curves, summarizing competitive inhibition experiments, that yield IC$_{50}$s that show the 4X peptide (SEQ ID NO:12) binds hTBPc (SEQ ID NO:3) 250 times tighter than the 2X peptide (SEQ ID NO:11). In order to quantitate the solution kinetics of hTBPc binding to synthetic 4X peptides (4 tandem repeats of DFDLDMLG) (SEQ ID NO:12) or 2X peptides (2 repeats), (SEQ ID NO:11) aliquots of hTBPc (124 nM) were incubated with increasing concentrations of either peptide at 4° C. for 1 hour. The mixtures were then separately injected over identical SAMs that were pre-bound with GST-4X (SEQ ID NO:14). Percent inhibition is plotted against the concentration of the blocking peptide in solution. 0% inhibition was taken to be the amount of hTBPc that bound to GST-4X surfaces when it was incubated with buffer alone. Background levels of binding were determined by injection of protein mixtures over naked GST surfaces. An IC$_{50}$ of 370 nM and 90 μM describe the equilibrium kinetics of hTBPc binding to 4X and 2X peptides, respectively.

Figure 7:
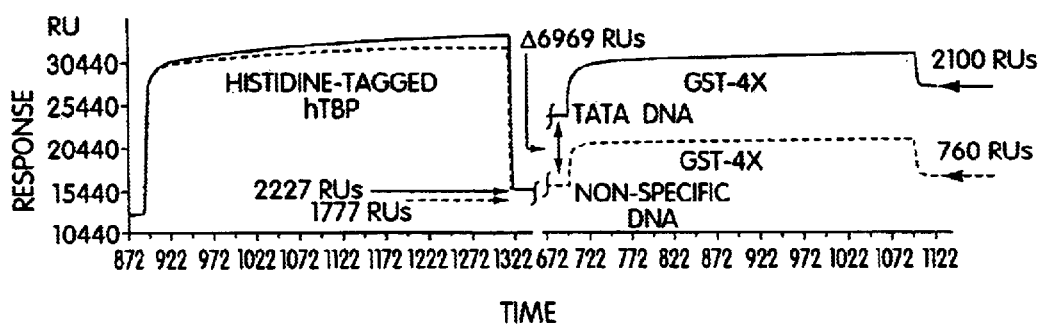
FIG. 7 shows that TATA sequence DNA bound to hTBP (SEQ ID NO:12) does not inhibit the interaction of hTBP with GST-4X (SEQ ID NO:14).

FIG. 7 shows that TATA sequence DNA bound to hTBP (SEQ ID NO:2) does not inhibit the hTBP/GST-4X interaction. N-terminally histidine-tagged hTBP (SEQ ID NO:15) was bound to NTA-SAMs and the mass of bound protein was quantitated and recorded by a BIAcore SPR instrument. The SAMs, bound with hTBP, were then removed from the instrument and separately incubated at RT for 15 minutes with solutions containing equal mass amounts of either DNA bearing the hTBP TATA recognition sequence or random sequence DNA (150 MM NaCl; 50 nanomoles DNA). The SAMs were then washed in running buffer and re-docked in the SPR instrument. The increase in absolute RUs of the baseline indicated that the TATA sequence DNA bound to surface immobilized hTBP with roughly 1:1 stoichiometry while the random DNA bound only nonspecifically. Protein plugs of GST4X (SEQ ID NO:14) were separately injected over these surfaces; the presence of DNA, bound nonspecifically or specifically, was not inhibitory to the subsequent binding of GST-4X to hTBP. Additionally, the measured association and dissociation rates, which were not affected by DNA-binding, were identical to those measured with GST-4X bound to the SAM and TBP in solution.

FIG. 8 shows that there is a synergistic increase in affinity between hTBPc (SEQ ID NO:3) in solution and surface-bound GST-2X when the density of immobilization is increased from 3.8% to 5.7%. Low (3.8% NTA) then high (5.7% NTA) density SAMs were docked in an SPR device. Histidine-tagged GST-2X (SEQ ID NO:13) and GST-4X (SEQ ID NO:17) fusion proteins (0.3 mg/ml) were separately immobilized on individual flow cells of the SAMs. The mass of the immobilized species is recorded in resonance units (RUs), where 1000 RUs=1 ng protein/mm$^2$. One RU results from a net change of 1/10,000 of a degree in the angle of minimum reflectance off of the differential dielectric interface of the sensing wave. hTBPc (SEQ ID NO:3) (124 nM) was then injected over the derivatized surfaces. The mass of the captured analyte was obtained by taking the difference between RUs recorded 10 seconds prior to and 25 seconds after the injection. When GST-2X (SEQ ID NO:13) was immobilized at low density it was not able to bind hTBP. However, when immobilized at slightly higher density, a high affinity interaction resulted. The stoichiometry of surface immobilized GST4X (SEQ ID NO:14) binding to hTBPc (SEQ ID NO:3) was relatively constant but, notably, twice that of GST-2X binding to hTBPc which reinforces the idea that two -2X ligands bind one hTBPc molecule.

FIG. 9 shows competitive inhibition experiments in which 2X ligands behave very differently in solution than when surface immobilized and that reiterated minimal activation motifs effectively compete for the same binding site(s) on hTBP (SEQ ID NO:2) as the parent protein. Histidine-tagged GST-4X (SEQ ID NO:17) or GST-2X (SEQ ID NO:16) were separately immobilized on NTA-SAMs docked in a BIAcore SPR instrument. hTBPc(residues 155–335) or hTBP (full length) was pre-incubated at high concentration (35 μM) with either buffer, a synthetic 2X peptide (SEQ ID NO:11) (X=DFDLDMLG) at 1:4 stoichiometry, a 4X peptide at (SEQ ID NO:12) 1:2 stoichiometry or a 1X-linker-1X peptide DFDLDMLG-((Ser)$_4$Gly$_1$)$_3$-DFDLDMLG) (SEQ ID NO:19) at 1:2 stoichiometry for 1 h at 40° C. Just prior to injection over the derivatized surfaces, the pre-incubation mixtures were diluted such that the final hTBP concentration was (124 nM). The synthetic 4X and 1X-linker-1X peptides blocked the interaction of hTBP with surface immobilized ligands but 2X peptides were not inhibitory. Histidine-tagged Gal4(1147)+VP16 (413–490) (SEQ ID NO:20) were similarly immobilized on NTA-SAMs. hTBP (SEQ ID NO:2) was preincubated, as described above, with either buffer or 4X peptide (SEQ ID NO:12) then diluted and injected over the VP16 presenting surfaces. The 32 amino acid 4X peptide effectively blocked the interaction of hTBP with the 78 amino acid VP16 activation domain.

A panel of variable density NTA-SAMs were prepared by diluting the concentration of the active component, NTA-thiol, relative to that of the inert component, EG$_3$-thiol, in ethanol solutions. Gold-coated glass slides were incubated in solutions containing 1.3%, 3.8%, 5.7%, or 11.4% NTA-thiol, with the total thiol concentration constant at 1 mM. The SAMs were glued onto blank CM-5 SPR chip cassettes and docked into a BIAcore instrument. A 16-mer peptide comprised of two repeats of the eight amino acid minimal activation motif (X=DFDLDMLG), (SEQ ID NO:10) derived from the human activator VP16, (SEQ ID NO:5) was fused to histidine-tagged GST (GST-2X) (SEQ ID NO:16). The fusion proteins were then immobilized on variable-density SAMs through complexation of the NTA group by the protein's histidine tag. This generated a series of surfaces that displayed peptides at incrementally decreasing distances from each other. The core region of human TBP (hTBPc: residues 155–335) (SEQ ID NO:3) (Nikolov et al., 1995) was injected over the peptide surfaces. GST-2X (SEQ ID NO:13) immobilized at low density (1.3%–3.8%), was unable to bind hTBPc. In contrast, when the same concentration hTBPc was injected over a more dense (5.7%–11.4%) GST-2X surface, where the average distance between peptide motifs would be smaller, a high affinity interaction resulted (see FIGS. 2 and 8). As a control, fusion proteins bearing four iterations of the minimal motif (GST-4X) (SEQ ID NO:14) were immobilized on the different density SAMs and assayed for the ability to bind the target molecule. Human TBPc, in solution, bound identically to GST-4X surfaces irrespective of the peptide density (see FIG. 3 and FIG. 8).

As the graph of FIG. 4 shows, the stoichiometry of hTBPc binding to GST-4X derivatized surfaces is a constant, independent of the immobilization density. In contrast, the binding of hTBPc to GST-2X surfaces is a non-linear function of the surface density. Notably, at corresponding surface concentrations, GST-2X bound half as much hTBPc as GST-4X, suggesting that two 2X modules (SEQ ID NO:11) immobilized at close proximity to each other (high density) simultaneously contact one hTBPc molecule. Kinetic rate constants were extracted by analyzing association and dissociation phases of sensorgram curves using a non-linear regression curve fitting program: BIAevaluation, version 2.1. The analysis assumed pseudo-first order reactions. The interaction between GST4X and hTBPc was characterized by an average association rate of $2.5 \times 10^4$ s$^{-1}$ M$^{-1}$ and an average dissociation rate of $4 \times 10^{31}$ $^4$ s$^{-1}$, yielding a calculated average k$_d$ of $16 \times 10^{-9}$ M. Standard errors obtained for each SPR experiment were considerably smaller than the variation in kinetic rates measured among several experiments using a wide range of NTA concentrations. There could be as much as a two-fold variation in the calculated k$_d$. Sensorgram association curves from the binding of hTBPc to GST-2X could not be fit by pseudo first order kinetics, again consistent with the idea that two -2X modules bind one hTBPc molecule. However, the dissociation phase of the sensorgram was well fit and yielded an average k$_d$ of $1.5 \times 10^{-3}$ +/−0.13 s$^{-1}$ for the interaction. The almost ten-fold difference between the 4X k$_d$ and 2X k$_d$ may indicate that the 2X dissociation curve is the superposition of two decay rates, corresponding to two dissociating species.

Note that at-high NTA density, the chip surface acted as a rigid linker between two -2X modules (SEQ ID NO:11) to mimic a 4X (SEQ ID NO:12) module, thus creating a higher affinity ligand. Three possible models might explain why the 4X (SEQ ID NO:12) peptide is higher affinity ligand for hTBPc (SEQ ID NO:3) than a 2X (SEQ ID NO:11) peptide (See FIG. 5). Model 1 proposes that the 4X peptide is a "bivalent" ligand that simultaneously and cooperatively binds more than one site on the target protein, producing a high affinity interaction characterized by a slower off-rate (Jencks, W. P. 1981. On the attribution and additivity of binding energies. *Proc. Natl. Acad Sci. USA.* 78(7): 4046–4050.). Model 2 says the binding of one recognition motif causes an allosteric effect that enhances the binding of subsequent motifs. Four connected minimal motifs provide for an increased local concentration of ligand available for the second higher affinity interaction. Model 3 proposes that the higher affinity interaction is the result of the summation of multiple interactions of equal strength between the target protein and the entire length of the peptide. A prediction of Model 1 is that 2X peptides, free in solution, will interact with hTBPc independently and exhibit a faster off-rate which is characteristic of monovalent binding. Therefore, if hTBPc is pre-bound by peptide in solution, the 4X peptide should be a much better inhibitor of hTBPc binding to surface immobilized ligand than the 2X peptide. Model 2 predicts that hTBPc pre-bound by 4X or 2X peptides (at twice the concentration) would be similarly inhibited, so long as incubation concentrations were high enough to compensate for the 4X local concentration advantage. Model 3 implies that mutation of amino acids within the peptide would decrease its affinity for TBP as an approximately linear function of the number of mutations.

In order to compare dissociation rates, aliquots of hTBPc were pre-incubated at very high concentration (35 $\mu$M) with either buffer, 2X peptide (1:4 stoichiometry), or 4X peptide (1:2 stoichiometry), then diluted to the usual hTBPc concentration 1, (124 nM) before injection over GST-4X (SEQ ID NO:13) surfaces. Synthetic 2X (16-mer) and 4X (32-mer) peptides were used to eliminate possible interference from GST. FIG. 9 shows that the preincubation of hTBPc with 2X peptide was in no way inhibitory to its interaction with surface immobilized GST-4X. In contrast, preincubation of hTBPc with 4X peptide (SEQ ID NO:12) completely abolished the interaction. Additional experiments showed that the 32-mer, but not the 16-mer peptide, also blocked the binding of hTBPc to high density GST-2X surfaces, again demonstrating that GST-2X, immobilized at high density, behaves like GST-4X.

The experiments tabulated in FIG. 9 argue against the allosteric effect model but are consistent with Models 1 and 3. The question is, does the increased binding energy of the hTBP-4X interaction result from the cumulative effect of multiple bonds along the length of the peptide or from the synergistic effect of two minimal motifs simultaneously binding to the target molecule, with the intervening amino acids merely serving as a tether between the two? A synthetic 31 amino acid peptide consisting two minimal motifs (DFDLDMLG) (SEQ ID NO:11) separated by a flexible linker ((Ser$_4$ Gly$_3$) (SEQ ID NO:18) was generated. This peptide, 1X-linker-1X, (SEQ ID NO:19) when preincubated with hTBP (SEQ ID NO:2) (under the same conditions described above) inhibited by 83% the complex's ability to bind to surface immobilized GST-4X (see FIG. 9). These results reinforce the premise of Model 1 and imply that the enhanced strength of binding between hTBP and the 4X peptide is due to a synergistic effect caused by two connected minimal activation motifs simultaneously binding to two separate and discrete sites on hTBP. One may also infer, from the last experiment, that the interaction between minimal activation motifs and hTBP is specific.

Next the kinetics of the surface interaction to analogous interactions in solution were compared. A series of equilibrium inhibition experiments were performed to characterize the solution interactions between hTBPc (SEQ ID NO:3) and 2X or 4X (SEQ ID NO:11) peptides. Aliquots of hTBPc, (124 nM), were mixed with increasing amounts of synthetic 2X or 4X peptide then incubated at 4° for 1 hour prior to injection over GST4X surfaces. Titration curves (see FIG. 6) yield an IC$_{50}$ of 370nM for the 4X peptide and 90 $\mu$M for the 2X peptide binding to hTBPc. In summary, the 4X peptide binds hTBPc about 250-times better than the 2X peptide. This is the relative difference between monovalent and bivalent binding of hTBPc. The interaction between the 4X peptide and hTBPc in solution is about 20-times weaker than the comparable surface interaction where diffusion is limited.

The physiological relevance of the interaction between hTBP and the reiterated minimal motifs was investigated. It has been argued that the widely observed in vitro interactions between TBP and activation domains are artifacts resulting from a nonspecific interaction between TBP's basic DNA-binding region and the acidic peptides. To rule out this possibility, N-terminally histidine-tagged hTBP (SEQ ID NO:15) was immobilized on NTA-SAMs then separately incubated with either: a) TATA sequence DNA; or b) DNA that did not contain a hTBP recognition sequence. GST-4X was then injected over the derivatized surfaces. DNA that did not contain a TATA sequence did not bind to the immobilized hTBP significantly. DNA containing a TATA sequence bound to immobilized hTBP with approximate 1:1 stoichiometry but was in no way inhibitory to the subsequent binding of GST-4X (SEQ ID NO:14) (see FIG. 7). In fact, hTBPc (SEQ ID NO:3) complexed by its cognate DNA bound roughly twice as much GST-4X as the uncomplexed hTBPc. This result is consistent with the observation that hTBPc exists as a dimer that is disrupted upon DNA binding (Taggart, A. K. P. and B. F. Pugh. 1996. Dimerization of TFIID when not bound to DNA. *Science.* 272:1331–1333.). The binding of an activating region does not seem to disrupt hTBPc dimerization.

A competitive inhibition experiment was performed to determine whether the 4X peptide (SEQ ID NO:12) could block the interaction between hTBP (SEQ ID NO:2) and the native activation domain of VP16 (SEQ ID NO:5). A histidine tagged Gal4(1–147)+VP16(413–490) (SEQ ID NO:20) fusion protein was immobilized on NTA-SAMs. hTBP was incubated with buffer or 4X peptide then injected over VP16 derviatized surfaces. The last two lines of FIG. 9 show that preincubation of hTBP with the 4X peptide (32 amino acids) completely abolished the hTBP-VP 16 (78 amino acids) interaction. This result is consistent with the idea that minimal activation motifs recognize the same binding site(s) on hTBP as the parent activator.

In conclusion, SAMs were used to form biospecific rigid, nano-scale probe arrays of known surface density and then utilized to determine the number of binding sites on a target molecule and an approximate distance between sites. This approach is not hampered by the vagaries of secondary or tertiary structures that would be encountered by using DNA or peptide spacers to determine distances between active sites. SPR was used to show that the avidity between TBP, in solution, and surface immobilized peptides was a non-linear function of peptide surface density.

Peptides immobilized on a 3.8% NTA-SAM were not able to bind hTBP, while peptides presented on a 5.7% NTA- SAM bound TBP with nano-molar affinity. The findings are consistent with the idea that this large increase in binding strength marks the transition between mono- and bivalent binding of the target protein. Individual 8 amino acid minimal activation motifs separated by a 15 amino acid flexible linker bound hTBP nearly as well as four tandem repeats of the motif, leading to the conclusion that hTBP has at least two discrete sites capable of simultaneously interacting with the 8 amino acid motif. Calculations based on an assumed Poisson distribution of NTA in the SAM indicate that the surfaces that did not bind hTBP (3.7% NTA) presented peptides an average distance of 29 Å apart while peptides in denser arrays (5.7% NTA) that bound hTBP with high avidity were on average 2 Å apart.

The crystal structure of hTBPc (SEQ ID NO:3) has been solved (Nikolov et al., 1995). The peptide consists of two imperfect repeats that form a two-domain saddle shaped DNA-binding protein with two-fold intramolecular symmetry. TBP binds DNA with the concave underside of its "saddle" shape. The general transcription factor TFIIB binds near the TBP/DNA complex at the downstream end leaving the convex "seat" of the to saddle available for other intermolecular interactions. Quasi-identical structures composed of basic helices and P sheets flank the seat of the saddle. Mirror image helices H2 and H2' are separated by distances on the order of 20 Å. It is conceivable that the minimal activation motifs, described herein, simultaneously bind to two-fold related pseudo-identical recognition sites that may be separated by approximately 23 Å.

Similar schemes can be devised to determine distances between active sites on other bivalent molecules or complexes. Of particular interest are dimeric hormone receptors whose signaling activity depends on its association state. Detailed knowledge of distances between active sites would allow for the rational design of agonist or antagonist drugs.

Experimental Methods

Protein preparation: hTBPc was prepared according to Nikolov et al., 1996 and full length histidine-tagged hTBP (SEQ ID NO:15) according to Lee et al. [Lee, W. S., C. C. Kao, G. O. Bryant, X. Liu and A. J. Berk. (1991) Adenovirus E1A activation domain binds the basic repeat in the TATA box transcription factor *Cell* 67:365–376]. Glutathione S-transferase (GST) fusion proteins (SEQ ID NO:9) were prepared according to Tanaka, 1996. The preparation of Gal4-VP 16 is described by Hori, R., S. Pyo and M. Carey, 1995. Protease footprinting reveals a surface on transcription factor TFIIB that serves as an interface for activators and co-activators. *Proc. Nati. Acad Sci. USA.* 92(13): 6047–6051.

DNA: TATA sequence DNA was prepared according to Parvin et al. [Parvin, J. D., R. J. McCormick, P. A. Sharp, and D. E. Fisher. 1995. Pre-bending of a promoter sequence enhances affinity for the TATA-binding factor. *Nature.* 373:724–727] with the exception that it was not circularized. A 50 base-pair double stranded oligo containing 2 Gal 4 binding sites, synthesized and quantitated by GibcoBRL, Life Technologies Inc., Grand Island, N.Y., was used as non-specific control DNA. Equal mass amounts of specific vs. non-specific DNA were added.

Synthetic peptides: Peptides were generated by F-MOC synthesis and quantitated by amino acid analysis, analytical HPLC and-mass spectroscopy.

The preparation self-assembled monolayers: NTA-SAMs were prepared according to Sigal et al., 1996. A panel of incrementally different density NTA surfaces was generated by serial dilution of a stock solution containing 11.4% NTA-thiol, relative to tri-ethylene glycol terminated thiol, into solutions containing the tri-ethylene glycol terminated thiol alone. Total thiol concentration was kept constant at 1 mM. NTA-SAMs were stored under argon for up to 1 week prior to use. Background levels of binding were assessed by passing reactants over underivatized GST surfaces and subtracted.

Surface plasmon resonance: Experiments were carried out in a BIAcore instrument at room temperature in phosphate buffered saline (PBS) (137 mM NaCl) running at a constant flow rate of 5 µl/min. Sample injection volumes (plugs) were 35 µl. Association and dissociation rate constants were extracted from the data with BIAevaluation software, version 2.1, assuming a pseudo first order kinetics model: $A+B \leftrightarrows AB$. Error rates were taken from the deviation of measurements among multiple experiments performed on surfaces of different NTA densities with a range of protein concentrations and using several different protein preparations, of the same species, to account for variation of the active concentration of a component.

Statistical calculations: Sulfur atoms bind to gold to form a face-centered hexagonal tiling pattern 4.99 Å on edge. In an ordered monolayer, all the positions of the hexagon are occupied by a thiol. Each vertex is shared by three hexagons, so there are three possible positions for thiol deposition per hexagon. If the thiol solution is doped with a derivatized species of thiol, such as ours is, the average number of NTA-thiols deposited per some number of hexagons ($\lambda$), can be calculated, assuming Poisson statistics, for a given NTA-thiol concentration. (It was assumed that the concentration of NTA-thiol in solution was equal to its concentration in the SAM; see FIG. 2 of Sigal et al., 1996). Equation (1) of FIG. 1 calculates how many hexagons, on average, must be filled before two NTA-thiols are deposited. For a 3.8% NTA-thiol concentration in solution, relative to $EG_3$-thiol, an average of 17.5 hexagons must be filled before 2 NTA ligands appear. For a 5.7% NTA solution, 11.7 hexagons must be filled before an average of two NTA ligands are deposited. The area of a hexagon 4.99 Å on edge is 64.69 Å$^2$ which is equal to the area of a square, 8.04 Å on edge. 17.5 hexagons would occupy the same area as a square $(17.5 \times 8.04^2)^{1/2}$ Å on edge, which equals 33.6 Å. Two NTA ligands were arbitrarily placed in a square representing 17.5 hexagons either 33.6 Å or 23.8 Å apart (See FIG. 1).

Since there are equal numbers of nearest and next-nearest neighbors, the average of these two distances is a first order approximation of the average distance between ligands resulting from a random distribution. According to this model, NTA ligands on SAMs formed from a 3.8% NTA-thiol solution would be an average of 29 Å apart, while NTA ligands in a SAM formed from a 5.7% NTA-thiol solution would be 23 Å apart. Calculations were done to evaluate the contribution of clustering using Poisson statistics.

Equation 2 calculates the probability, P, of having n NTA ligands per unit area, where $\lambda$, equals the average number of NTAs per unit area. Equation 3 calculates the ratio of the probabilities of having one NTA ligand to two NTA ligands deposited per unit area. It is 17-times more likely to get one NTA than two, per unit area, for 3.8% NTA-thiol SAMs and 11 times more likely at 5.7% NTA concentration.

$$P(n) = e^{-\lambda} \lambda^n / n! \qquad (2)$$

$$\frac{P(1)}{P(2)} = \frac{e^{-(3 \text{ sites})([0.038] \, NTA)}[(3)(0.038)]^1 / 1!}{e^{-(3 \text{ sites})([0.038] \, NTA)}[(3)(0.038)]^2 / 2!} \qquad (3)$$

All publications cited in this application are hereby incorporated by reference. The citation of any publication is for its disclosure prior to the filing date and should not be construed as an admission that the present invention is not entitled to antedate such publication by virtue of prior invention.

It is to be understood that the above invention is not limited to the particular embodiments described which are meant to be for illustrative purposes only. Variations and modifications of these embodiments may be made that are still included in the description of this invention and fall within the scope of the appended claims.

---

What is claimed is:

1. A method for determining distance between binding sites on a target molecule, comprising:
    contacting a target molecule with a self-assembled monolayer comprising binding moieties immobilized with respect to each other in controlled geometries, each of the controlled geometries having a predetermined density of immobilized binding moieties,
    identifying a controlled geometry with the lowest density of immobilized binding moieties that elicits a jump in affinity for the target molecule, and
    determining the distance between immobilized binding moieties in the controlled geometry with the lowest predetermined density of immobilized binding moieties to determine the distance between binding sites on the target molecule.

2. The method of claim 1, wherein each of the self-assembled monolayers incorporates at least one thiol species that is capable of directly or indirectly displaying a binding moiety to the target molecule and at least one inert spacer thiol component.

3. The method of claim 2, wherein the at least one thiol species and the at least one inert spacer thiol component are mixed in defined proportions before they are applied on a suitable substrate to form the self-assembled monolayer.

4. The method of claim 2, wherein determining the distance between immobilized binding moieties in the controlled geometry with the lowest predetermined density of immobilized binding moieties that elicits a jump in affinity for the target molecule comprises correlating changes in binding affinity to a density of the at least one thiol species, to determine a critical binding moiety density at which two or more of the immobilized binding moieties simultaneously interact with the target molecule.

5. The method of claim 4, wherein statistical calculations are applied to the critical binding moiety density and thiol packing dimensions to determine a probable distance between the immobilized binding moieties.

6. The method of claim 4, wherein statistical calculations are applied to the critical binding moiety density to determine a probable distance between binding sites on a target molecule or complex of molecules.

7. The method of claim 1, wherein extracted distance information is used in rational design of multi-valent drugs.

8. The method of claim 4, wherein surface plasmon resonance is used to measure binding affinities between immobilized binding moieties in controlled geometries and a target molecule in solution.

9. The method of claim 1, wherein the target molecule has biologically relevant activity.

10. The method of claim 9, wherein the target molecule is a protein.

11. The method of claim 10, wherein the target molecule is a protein complex.

12. The method of claim 1, wherein the immobilized binding moiety that contacts the target molecule is a biologically relevant binding partner of the target molecule or fragment thereof.

13. The method of claim 1, wherein the immobilized binding moiety that contacts the target molecule is a is a protein or fragment thereof.

14. The method of claim 1, wherein the immobilized binding moiety that contacts the target molecule is a small molecule.

15. The method of claim 14, wherein the small molecule is derived from a combinatorial drug library.

16. The method of claim 1, wherein the immobilized binding moiety that contacts the target molecule is a combination of small molecules.

17. The method of claim 1, wherein a mixed self-assembled monolayer is formed from a first, active component species and at least one other component.

18. The method of claim 17, wherein the at least one other component is an inert spacer component.

19. The method of claim 17, wherein the at least one other component species is a spacer molecule and an inhibitor of non-specific binding and has the formula X-R-O-$(CH_2CH_2-O)_n$-H, wherein X is a functional group that adheres to a suitable substrate, R is a spacer moiety that promotes formation of a self-assembled monolayer of a plurality of molecules, and n is a number form 1 to 10.

20. The method of claim 17, wherein the first, active component species is X-R-Ch-M, where
    X is a functional group that adheres to a suitable substrate,
    R is a spacer moiety that promotes formation, from solution, of a self-assembled monolayer of a plurality of molecules,
    Ch represents a chelating agent that coordinates a metal ion selected from the group consisting of bidentate, tridentate and quadradentate chelating agents, and M represents a metal ion coordinated to the chelating agent, and wherein M is also coordinated to a biological binding partner of a biological molecule via coordination sites not filled by the chelating agent that, upon exposure to a polyamino acid tag are able to become coordinated by the polyamino acid tag.

21. The method of claim 20, wherein the chelating agent is a quadradentate chelating agent.

22. The method of claim 20, wherein the chelating agent is nitrilotriacetic acid.

23. The method of claim 20, wherein the chelating agent and the metal ion are selected such that the chelating agent coordinates all but at least two of the metal coordination sites.

24. The method of claim 20, wherein the metal ion is $Ni^{2+}$.

25. The method of claim 20, further comprising a biological binding partner of a biological molecule coordinated to the metal ion.

26. The method of claim 25, wherein the biological binding partner includes a polyamino acid tag that coordinates the metal ion.

27. The method of claim 26, wherein the polyamino acid tag comprises at least two neighboring amino acids defining a chelating agent that coordinates the metal ion.

28. The method of claim 27, wherein the at least two of the neighboring amino acids are at least two histidines.

29. The method of claim 2, wherein the at least one thiol species is a nitrilo tri-acetic acid (NTA) terminated thiol that when complexed with $Ni^{2+}$ captures histidine tagged proteins or peptides, and the at least one inert spacer thiol component is an inert tri-ethylene glycol-terminated thiol.

30. The method of claim 3, wherein the defined proportions of the at least one thiol species and inert components of the self-assembled monolayer are such that the at least one thiol species components of the self-assembled monolayer are spaced on the suitable substrate at distances that promote cooperative-binding of attached therewith, immobilized binding moieties, to the target molecule.

31. The method of claim 3, wherein the suitable substrate is selected from the group consisting of gold-covered articles, gold articles and gold colloids.

* * * * *

UNITED STATES PATENT AND TRADEMARK OFFICE
CERTIFICATE OF CORRECTION

PATENT NO. : 6,723,517 B1
DATED : April 20, 2004
INVENTOR(S) : Bamdad

It is certified that error appears in the above-identified patent and that said Letters Patent is hereby corrected as shown below:

Column 52,
Line 36, please replace "is a is a" with -- is a --
Line 57, pleast replace "form" with -- from --

Signed and Sealed this

Thirty-first Day of August, 2004

JON W. DUDAS
*Director of the United States Patent and Trademark Office*